US009622657B2

United States Patent
Trese et al.

(10) Patent No.: US 9,622,657 B2
(45) Date of Patent: Apr. 18, 2017

(54) AUTOMATED SYSTEM FOR MEASUREMENT OF ZONE 1 IN ASSESSMENT OF SEVERITY OF RETINOPATHY OF PREMATURITY

(71) Applicants: Michael T. Trese, Novi, MI (US); Antonio Capone, Jr., Novi, MI (US); Kimberly Drenser, Novi, MI (US); Carl Park, Novi, MI (US)

(72) Inventors: Michael T. Trese, Novi, MI (US); Antonio Capone, Jr., Novi, MI (US); Kimberly Drenser, Novi, MI (US); Carl Park, Novi, MI (US)

( * ) Notice: Subject to any disclaimer, the term of this patent is extended or adjusted under 35 U.S.C. 154(b) by 0 days.

(21) Appl. No.: 14/968,622

(22) Filed: Dec. 14, 2015

(65) Prior Publication Data

US 2016/0213242 A1 Jul. 28, 2016

Related U.S. Application Data

(60) Provisional application No. 62/091,112, filed on Dec. 12, 2014.

(51) Int. Cl.
*A61B 3/14* (2006.01)
*A61B 3/00* (2006.01)
*A61B 3/12* (2006.01)
*A61B 5/00* (2006.01)

(52) U.S. Cl.
CPC .......... *A61B 3/0025* (2013.01); *A61B 3/0033* (2013.01); *A61B 3/1241* (2013.01); *A61B 5/0022* (2013.01)

(58) Field of Classification Search
USPC .................................................. 351/200–246
See application file for complete search history.

(56) References Cited

U.S. PATENT DOCUMENTS

| 8,090,164 B2 | 1/2012 | Bullitt et al. |
| 8,201,943 B2 * | 6/2012 | Hammer ............. A61B 3/1025 351/200 |
| 8,233,681 B2 | 7/2012 | Aylward et al. |

(Continued)

OTHER PUBLICATIONS

Williams, Steven L. et al. "Telemedical Diagnosis of Retinopathy of Prematurity: Accuracy of Expert vs. Non-expert Graders", NIH Public Access, Author Manuscript, Br J Ophthalmol. Mar. 2010 ; 94(3): 351-356. doi:10.1136/bjo.2009.166348.

(Continued)

*Primary Examiner* — Mohammed Hasan
(74) *Attorney, Agent, or Firm* — Avery N. Goldstein; Blue Filament Law PLLC

(57) ABSTRACT

An automated method for diagnosing and evaluating severity of retinopathy of prematurity in a retina of a patient is provided that is superior to conventional techniques. A graphical user interface (GUI) is provided for receiving biographical information for the patient creating a patient record in a database via the GUI. A photograph of the retina of the patient is collected and placed in the patient record via the GUI. The photograph is then analyzed to determine vascular distributions within the retina. A zone 1 boundary is assigned to the retina based on a set of threshold levels with respect to the determined vascular distributions. A system for performing the automated method is also provided.

14 Claims, 47 Drawing Sheets

(56) References Cited

U.S. PATENT DOCUMENTS

2013/0166313 A1* 6/2013 Kitfield ................ G06F 19/327
                                                         705/2

OTHER PUBLICATIONS

Abramoff, Michael D. et al. "Retinal Imaging and Image Analysis", IEEE transactions on medical imaging, NIH Public Access, Author Manuscript, IEEE Trans Med Imaging. Jan. 1, 2010; 3: 169-208.
Chiang, Michael F. et al. "Image Analysis for Retinopathy of Prematurity Diagnosis", NIH Public Access, Author Manuscript, J AAPOS. Author manuscript; available in PMC Oct. 1, 2010. J AAPOS. Oct. 2009 ; 13(5): 438-445. doi: 10.1016/j.jaapos.2009.08.011.

* cited by examiner

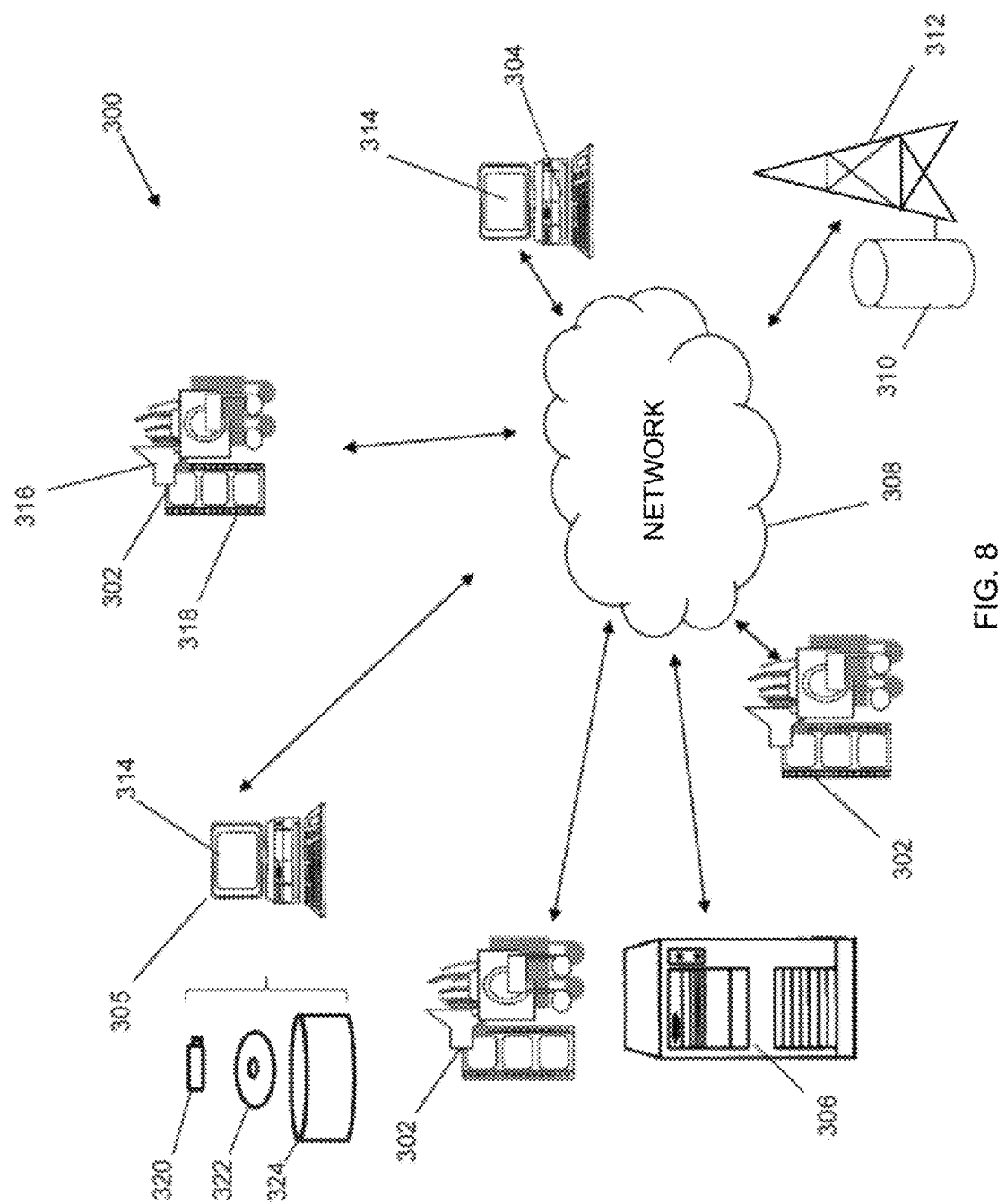

AUTOMATED SYSTEM FOR MEASUREMENT OF ZONE 1 IN ASSESSMENT OF SEVERITY OF RETINOPATHY OF PREMATURITY

RELATED APPLICATIONS

This application is a non-provisional application that claims priority benefit of U.S. provisional application Ser. No. 62/091,112; filed 12 Dec. 2014; the contents of which are hereby incorporated by reference.

FIELD OF THE INVENTION

The present invention in general relates to retinal disease diagnosis and in particular to an automated system and method for diagnosing and evaluating the extent of retinopathy of prematurity.

BACKGROUND OF THE INVENTION

The visible parts of the human eye 10, as shown in prior art FIG. 1, include the transparent cornea 12, the normally white sclera 14, the colored (blue, green, brown or a mixture of these) iris 16, and an opening in the iris, the normally black pupil. A ray of light, after passing through the cornea 12, which partially focuses the image, passes through the anterior chamber, the pupil, the lens 18, which focuses the image further, the vitreous and is then focused on the retina 20. The retina 20 is a very thin layer of tissue that lines the inner part of the eye 10. The retina 20 is responsible for capturing the light rays that enter the eye 10. The retina 20 is supported by its retinal pigment epithelium, which is normally opaque, the choroid and the sclera. The blood supply of the retina 20 is primarily through the choroid and secondarily through the retinal vasculature 22 which lies on top of the retina 20. The macula 24 is located roughly in the center of the retina 20, temporal to the optic nerve 26. The macula 24 is a small and highly sensitive part of the retina 20 responsible for detailed central vision. The light rays captured by retina are turned into impulses, and the impulses are transported to the brain via the optic nerve 24.

Retinopathy of prematurity (ROP) occurs in over 16% of all premature births. In babies weighing less than 1,700 grams at birth, over 50% will develop ROP. In the United States, over 2,100 children annually experience the complications of ROP, and of which 500 to 1,200 cases of new blindness or severe complications are reported. Studies have found that about 30% of infants with advanced ROP have 20/200 or less in their better eye.

It is known that the retinal area without adequate blood supply emits a chemical trigger (vascular endothelial growth factor) to stimulate growth of the abnormal vasculature. The abnormal vasculature leads to a formation of a ring of scar tissue attached to both the retina and the vitreous gel that fills the center of our eyes. As the scar contracts, it may pull on the retinal creating a retinal detachment.

In 1984, an international classification system was developed that classifies ROP by anatomical zones, clock dial like locations within the eye, and stages of severity. Zone 1 is the posterior of the retina while zone 3 is the far peripheral retina. The larger the number of clock hours of vessels ending in Zone 1, the higher the risk of blindness associated with ROP. Stage 0 is the mildest form of ROP while Stage 5 is the most severe indicating total retinal detachment. FIG. 2 depicts the zones used in the classification and the thresholds for treatment of ROP. Based on classification of the location and extent of the ROP a treatment regime may be prescribed.

Currently, the diagnosis of a patient's ROP condition using the classification system is a manual process that requires subjective judgments. It has been shown that manual designation of the zone 1 boundary varies considerably, while clinicians are generally accurate in identifying the location of the optic nerve and the center of the macula. The inaccurate determination of the extent of the zone 1 boundary leads less than optimal treatment selections.

Thus, while there have been many advances in the diagnosis and evaluation of diseases of the eye, there still exists a need for improved systems and methods that increase the diagnostic accuracy of the conditions, while removing the subjectivity of a physician evaluation.

SUMMARY OF THE INVENTION

An automated method for diagnosing and evaluating severity of retinopathy of prematurity in a retina of a patient is provided that is superior to conventional techniques. A graphical user interface (GUI) is provided for receiving biographical information for the patient creating a patient record in a database via the GUI. A photograph of the retina of the patient is collected and placed in the patient record via the GUI. The photograph is then analyzed to determine vascular distributions within the retina. A zone 1 boundary is assigned to the retina based on a set of threshold levels with respect to the determined vascular distributions. A system for performing the automated method is also provided.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIGS. 4A-4H are screen shots for inputting a patient photo information for analysis and diagnostic according to an embodiment of the invention;

FIG. 8 is a schematic diagram illustrating an overall view of communication devices, computing devices, and mediums for implementing embodiments of the invention.

The detailed description explains the preferred embodiments of the invention

DESCRIPTION OF THE INVENTION

The present invention has utility as an automated system and method for accurately diagnosing and evaluating the severity of ROP. A graphical user interface (GUI) is provided for inputting and creating a patient database that combines patient biographical information with high resolution retinal images that are suitable for disease diagnostics of the eye via automated analysis of the images. In a specific embodiment, automated diagnostics of the extent and severity of retinopathy of prematurity (ROP) is determined based on the analysis of retinal vasculature and related structures in the high resolution images, where the automated assignment of zones and quadrants indicates the location and extent of the ROP, and a treatment regime may be prescribed. Vascular distributions are used by the system to determine the automated assignment of zone 1 and in some embodiments, quadrants of the eye. In a specific embodiment machine learning and artificial intelligence (AI) may be utilized to provide diagnostic information based on a learned history of previous patient images and inputted expert analysis of the images by physicians and researchers. The present invention affords a consistent method of identifying the boundary of zone 1, and therefore accurately diagnosing the severity of ROP.

Figure 1:
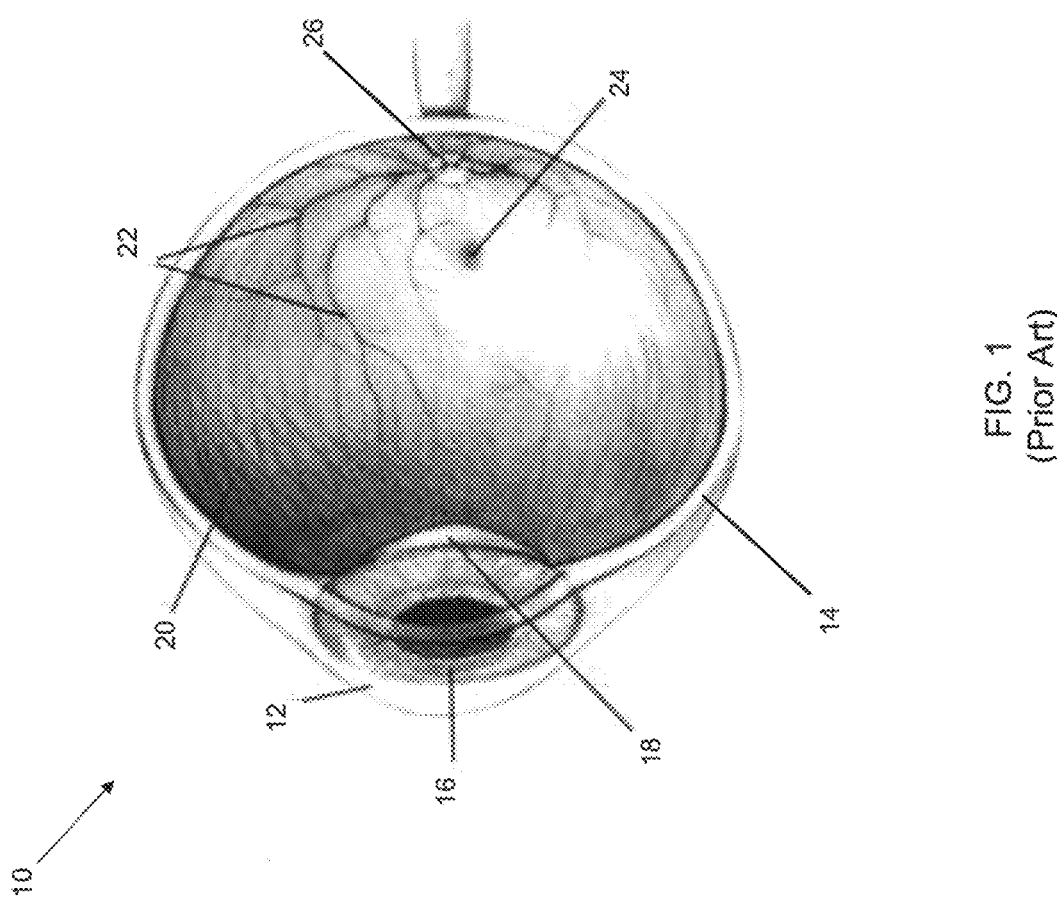
FIG. 1 is a prior art perspective cross sectioned view of the human eye.
Figure 2:
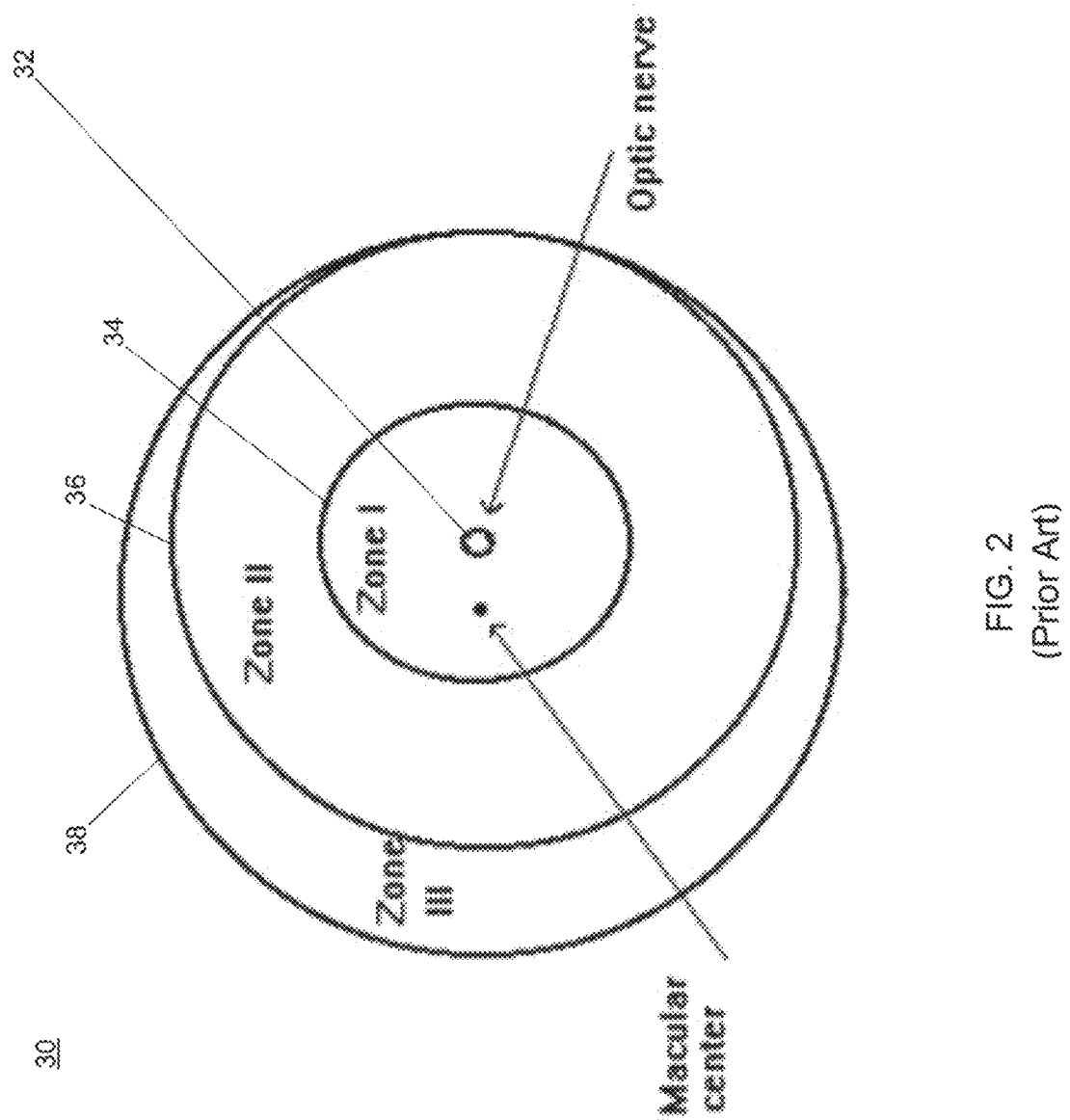
FIG. 2 depicts the prior art zones used in the classification and the thresholds for treatment of ROP.
Figure 3A:
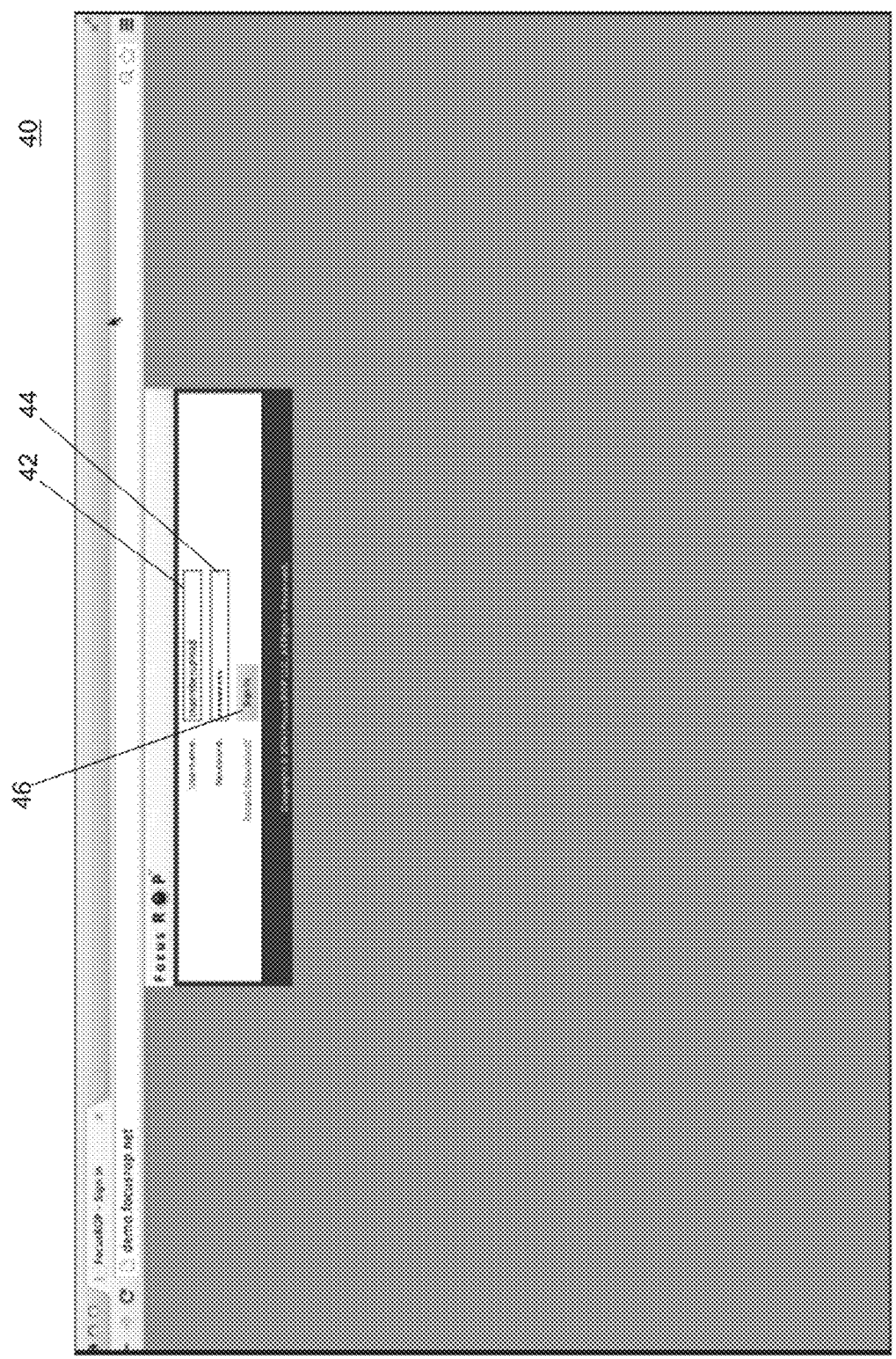
FIGS. 3A-3C are screen shots of the login screen and basic patient information input according to an embodiment of the invention.
Figure 3B:
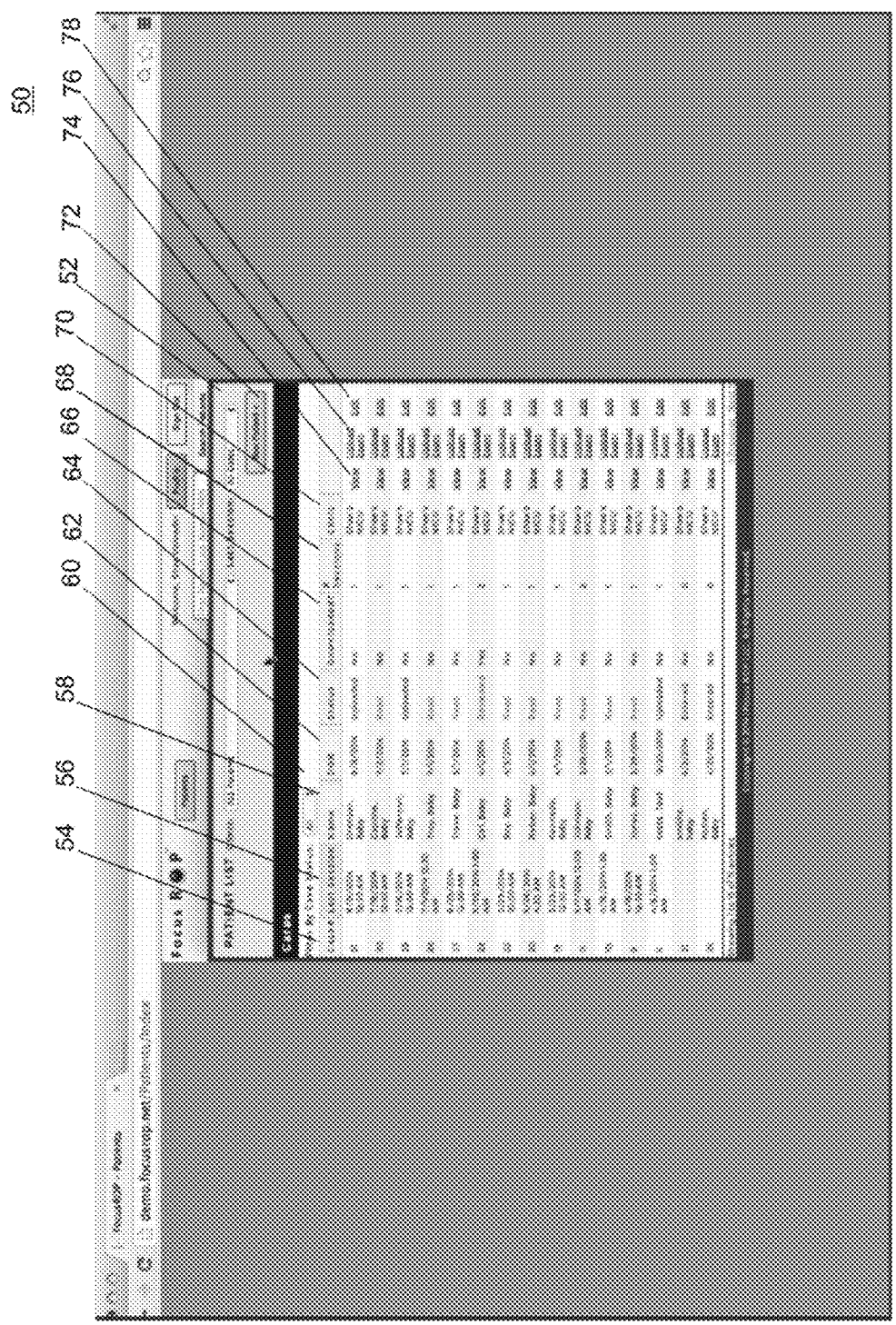
Figure 3C:
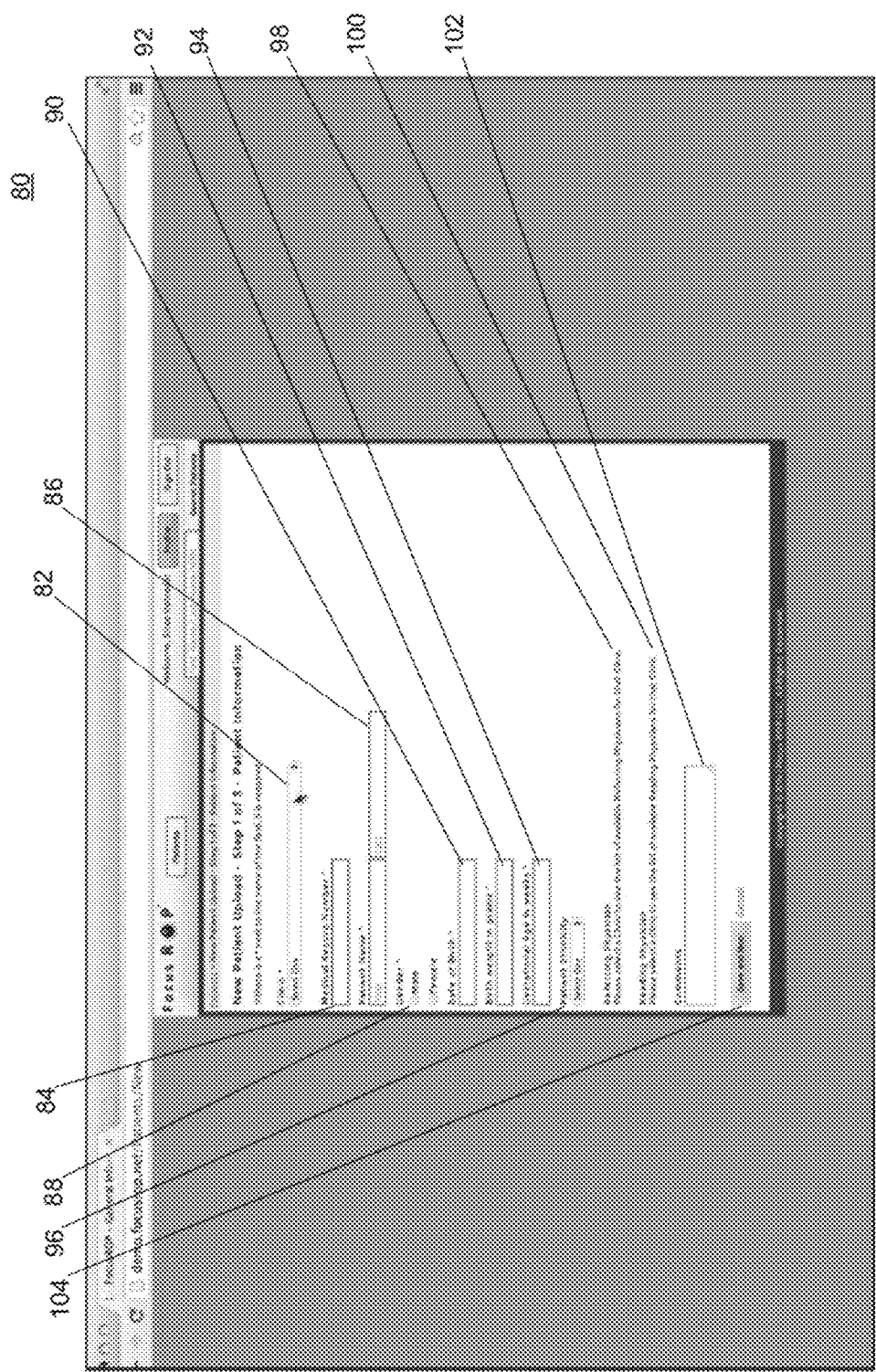

Software for tissue imaging operative a package onto which the present invention is programmed is detailed in U.S. Pat. Nos. 8,090,164; and 8,233,681. Referring now to the figures, FIGS. 3A-3C are a series of screen shots of the login screen and for basic patient information input according to an embodiment of the invention. As shown in FIG. 3A, a login screen 40 is shown with input fields for username 42, password 44, and a sign in button 46 that provides a user with access to the system when the username 42 and password 44 are authenticated by the system. Upon entry into the automated system a patient list screen 50 is shown to the user, where the patients shown in the list is based on filter settings 52. In a specific configuration of the patient list 50, patient information is further filtered based on case status 60, and is presented in tabular form with headers including case number 54, date/time of last session 56, patient name 58, date of birth (DOB) 62, status (information entered, uploaded, read, etc.) 64, downloaded (yes/no) 66, number of sessions 68, clinic where an examination occurred 70. Links including view 74 to view a patient's information, upload patient information 76, and to edit a patient profile or information 78. The new patient button 72 may be selected to add patients and their corresponding information to the database via patient biography input page 80. In FIG. 3C, patient biographical information is inputted and uploaded to the database in step one of a three step process. As shown in FIG. 3C a drop down menu 82 is provided to select the clinic where the patient was examined, and fillable input fields are also provided for a medical record number 84, patient name 86, gender 88, date of birth 90, birth weight 92, gestational age 94, patient ethnicity 96, referring physician based on clinic 98, reading physician 100, a fillable comments section 102.

Figure 4A:
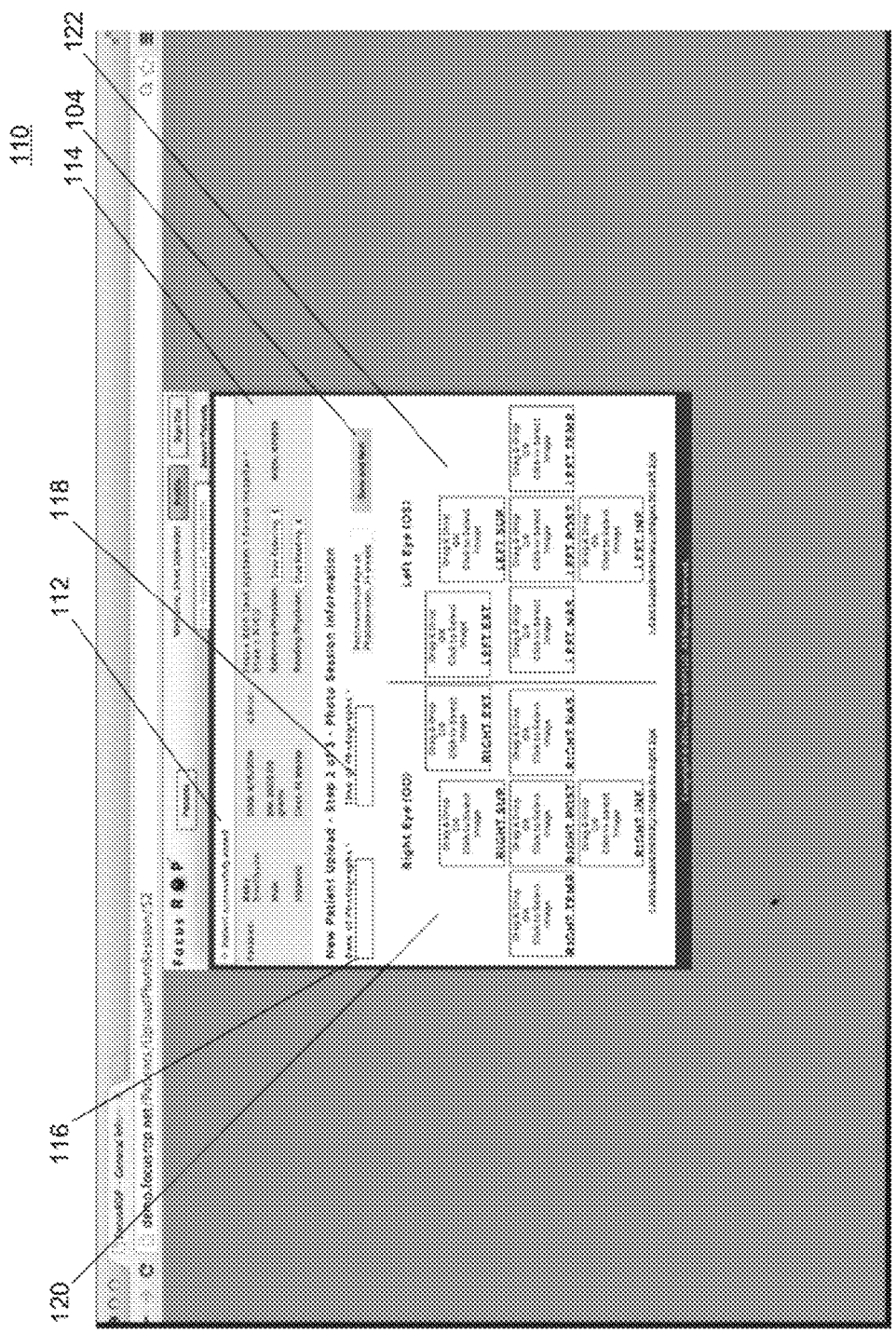
Figure 4B:
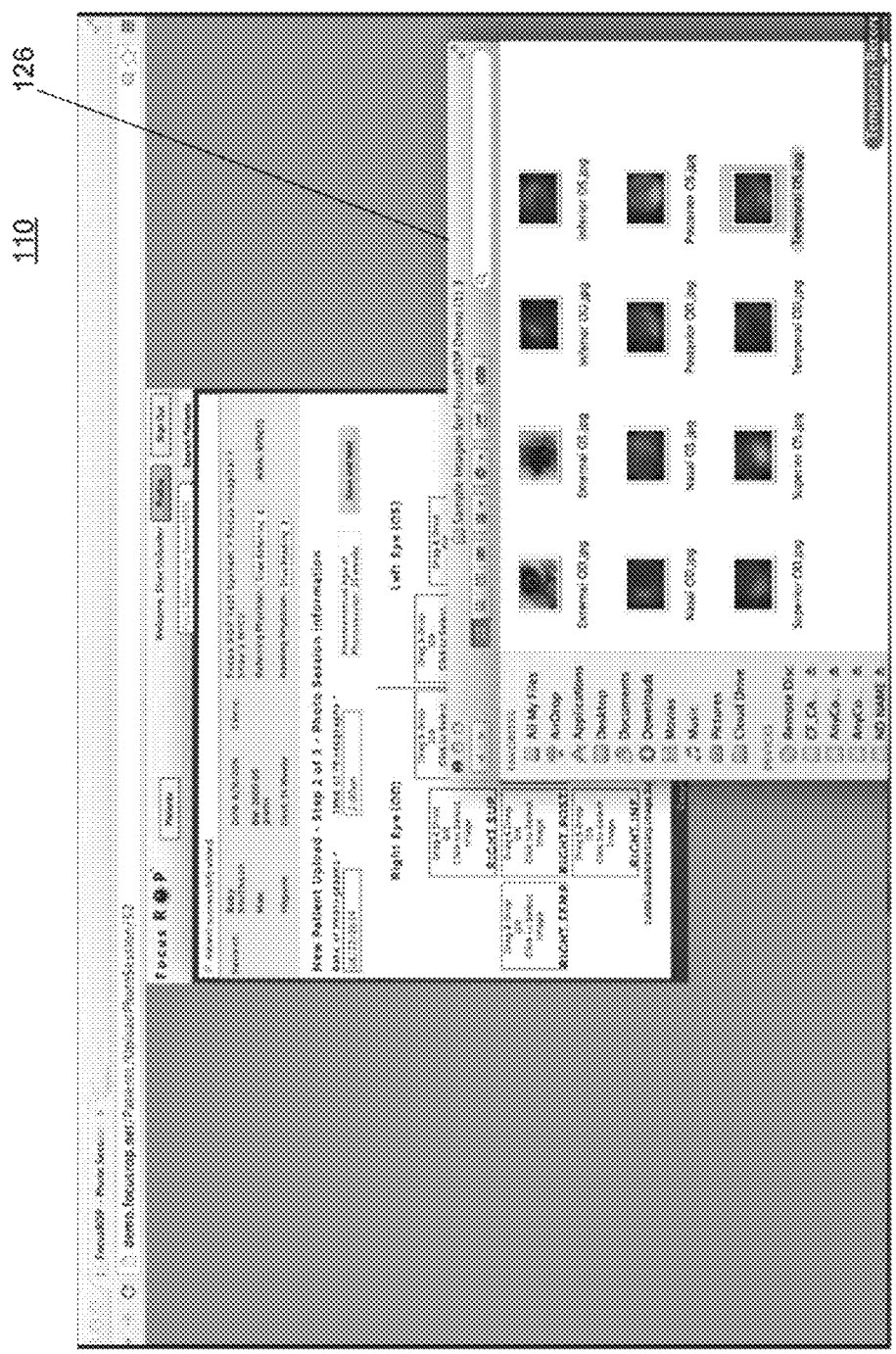
Figure 4C:
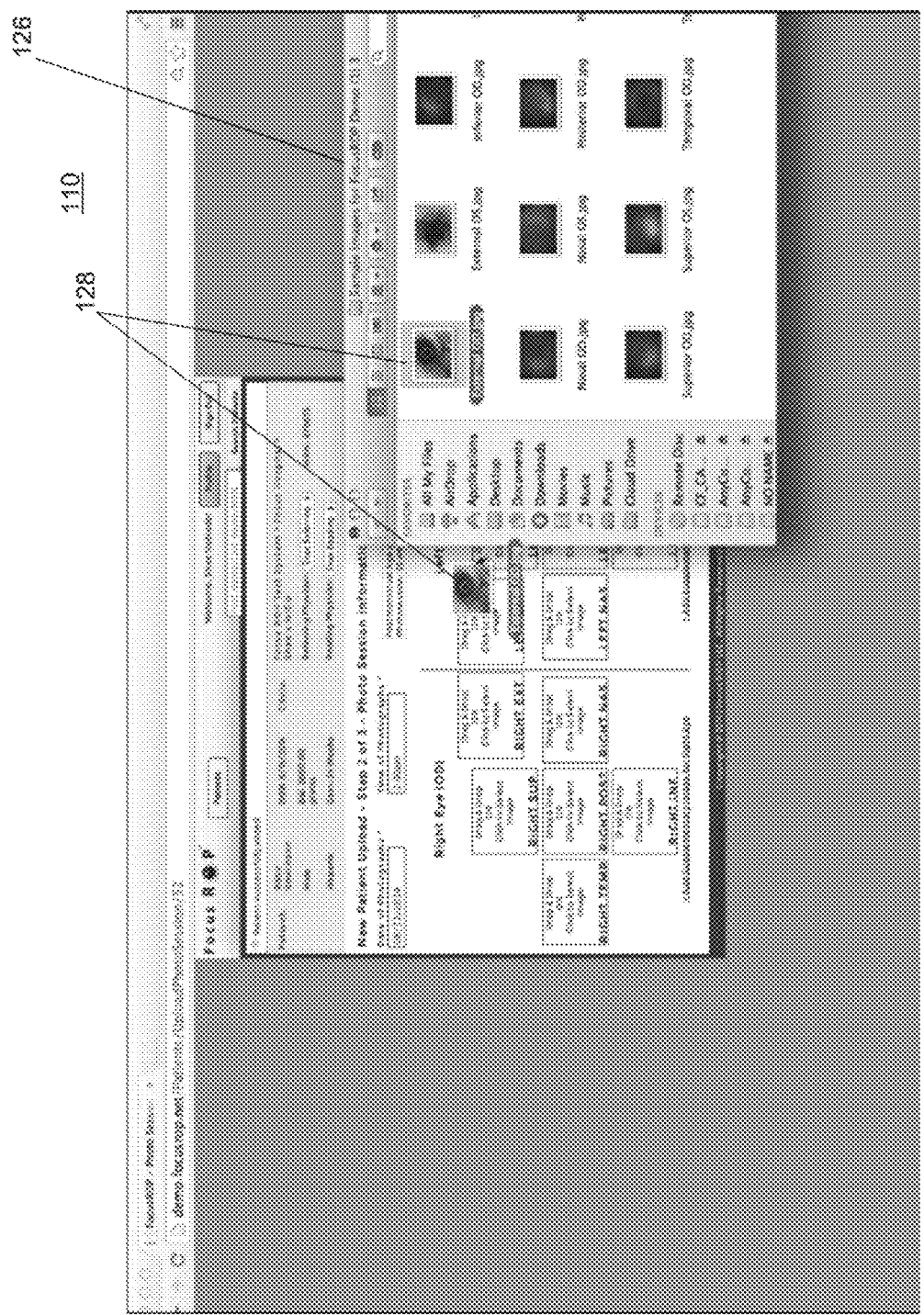
Figure 4D:
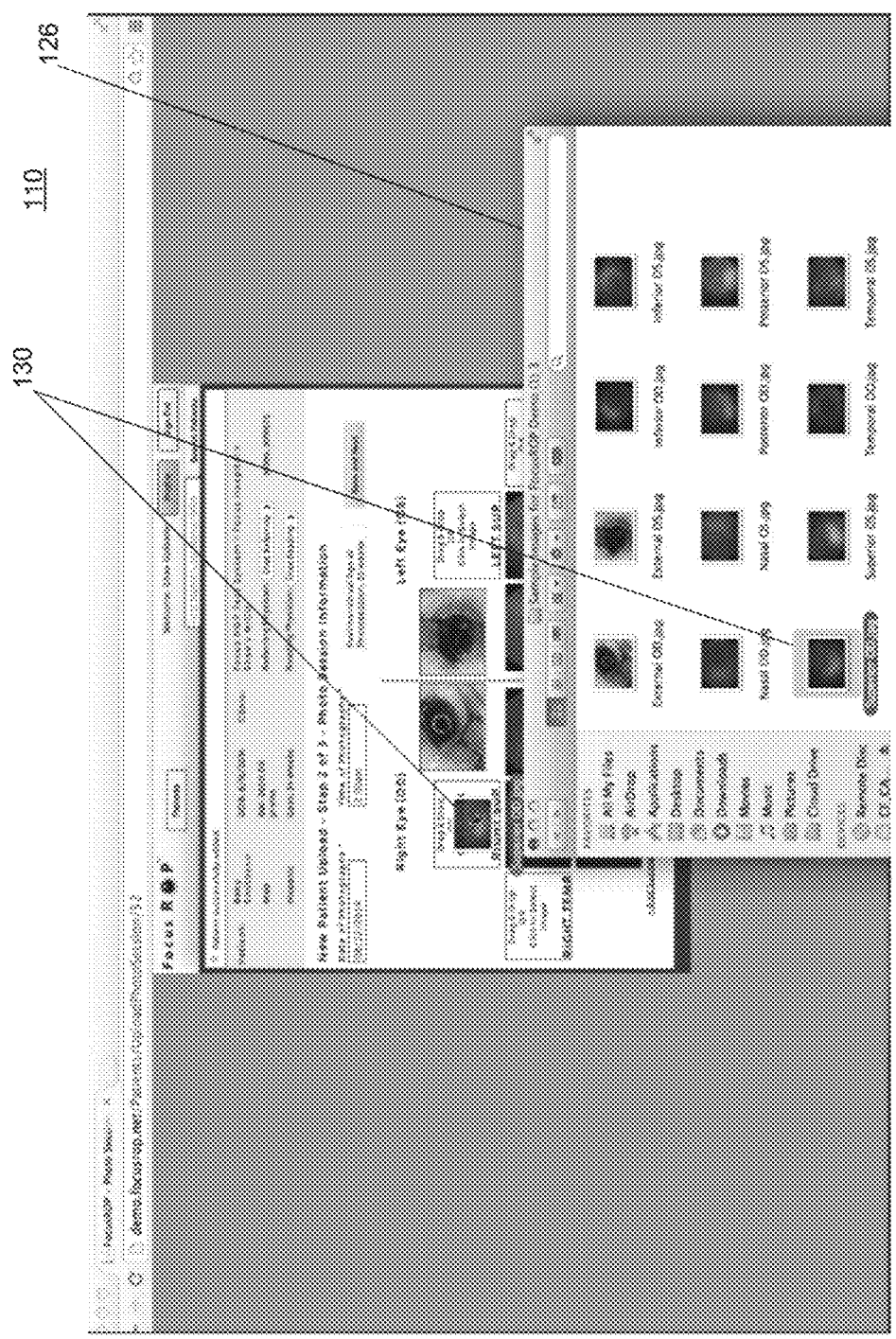
Figure 4E:
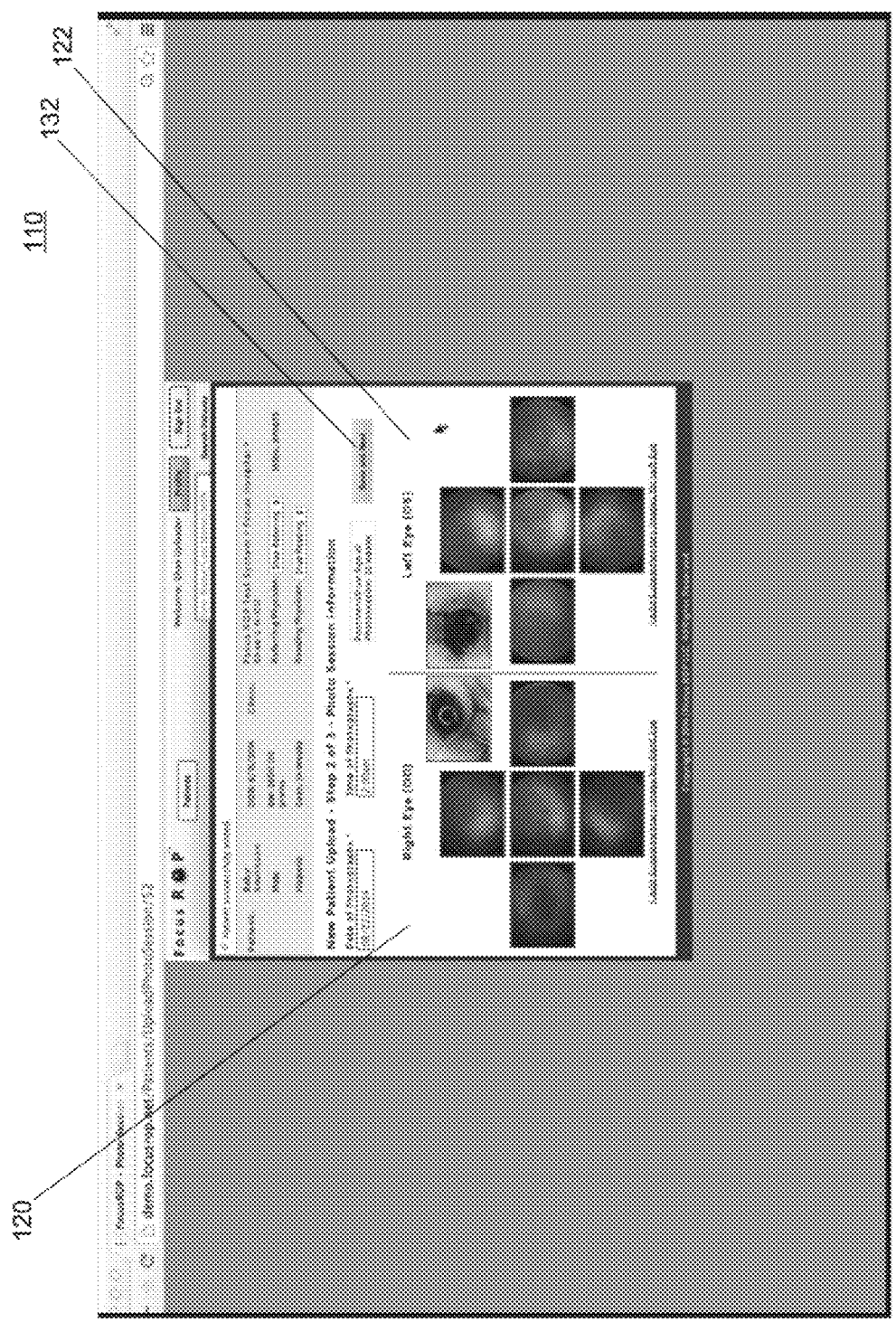
Figure 4F:
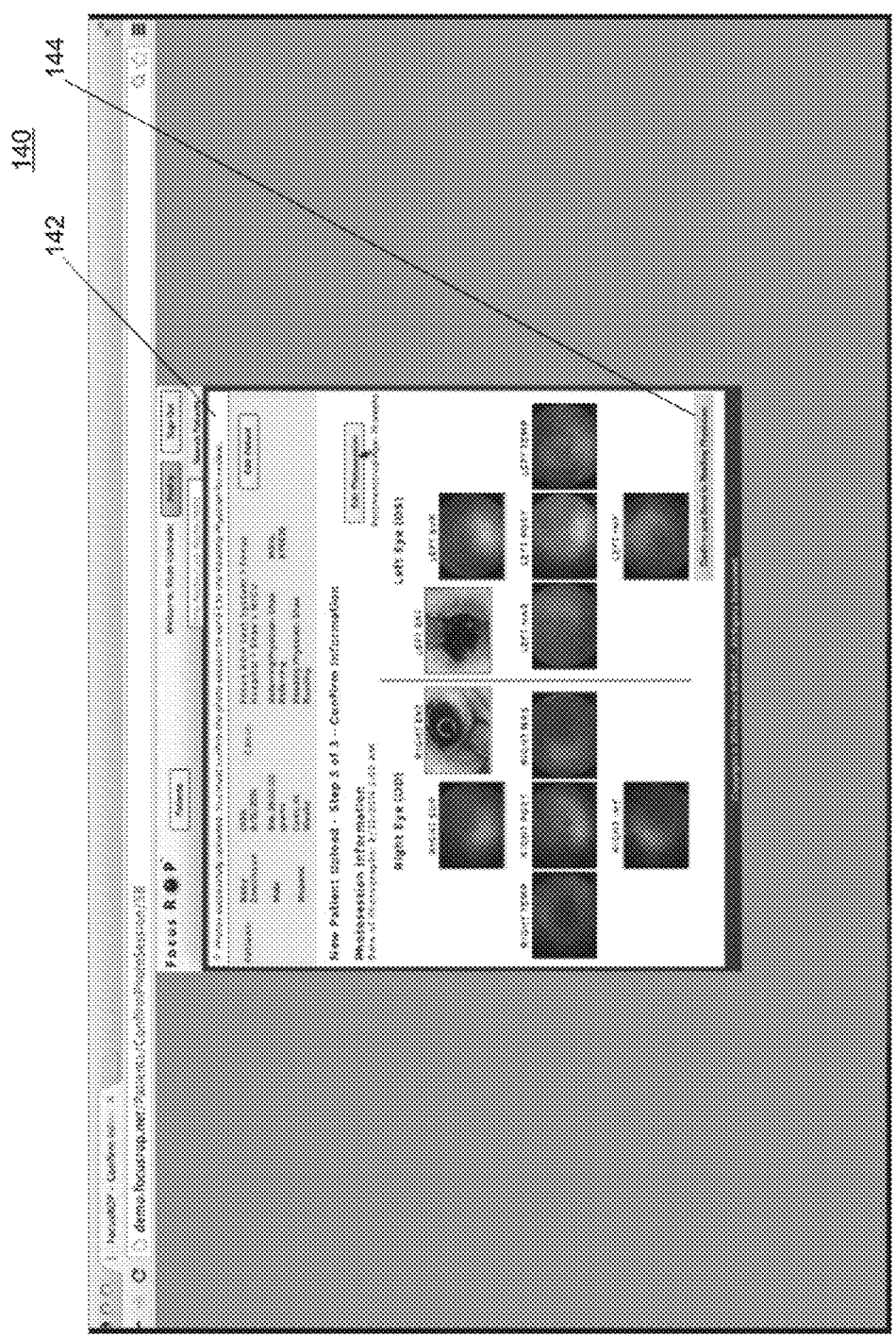
Figure 4H:
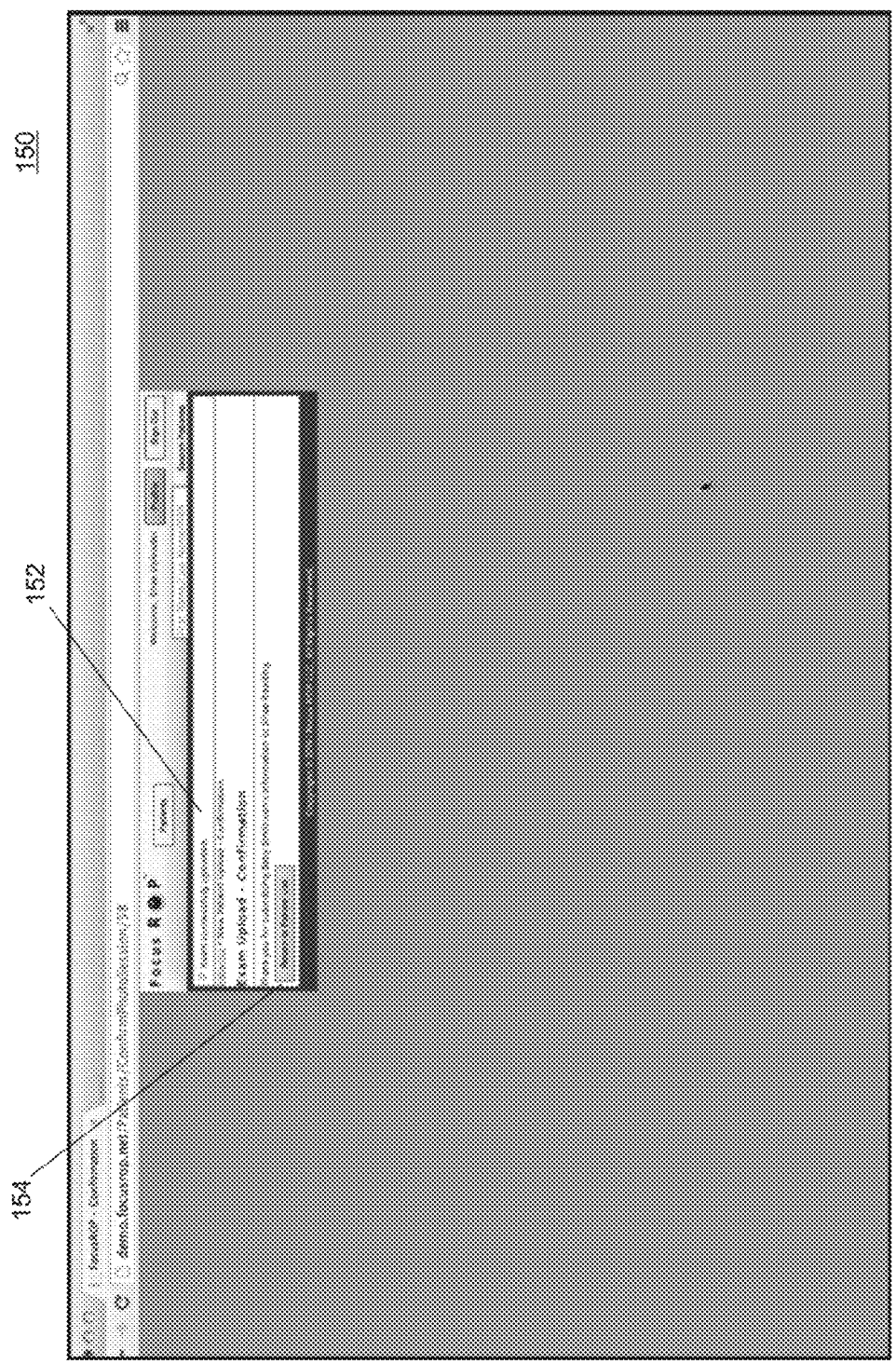
Figure 5A:
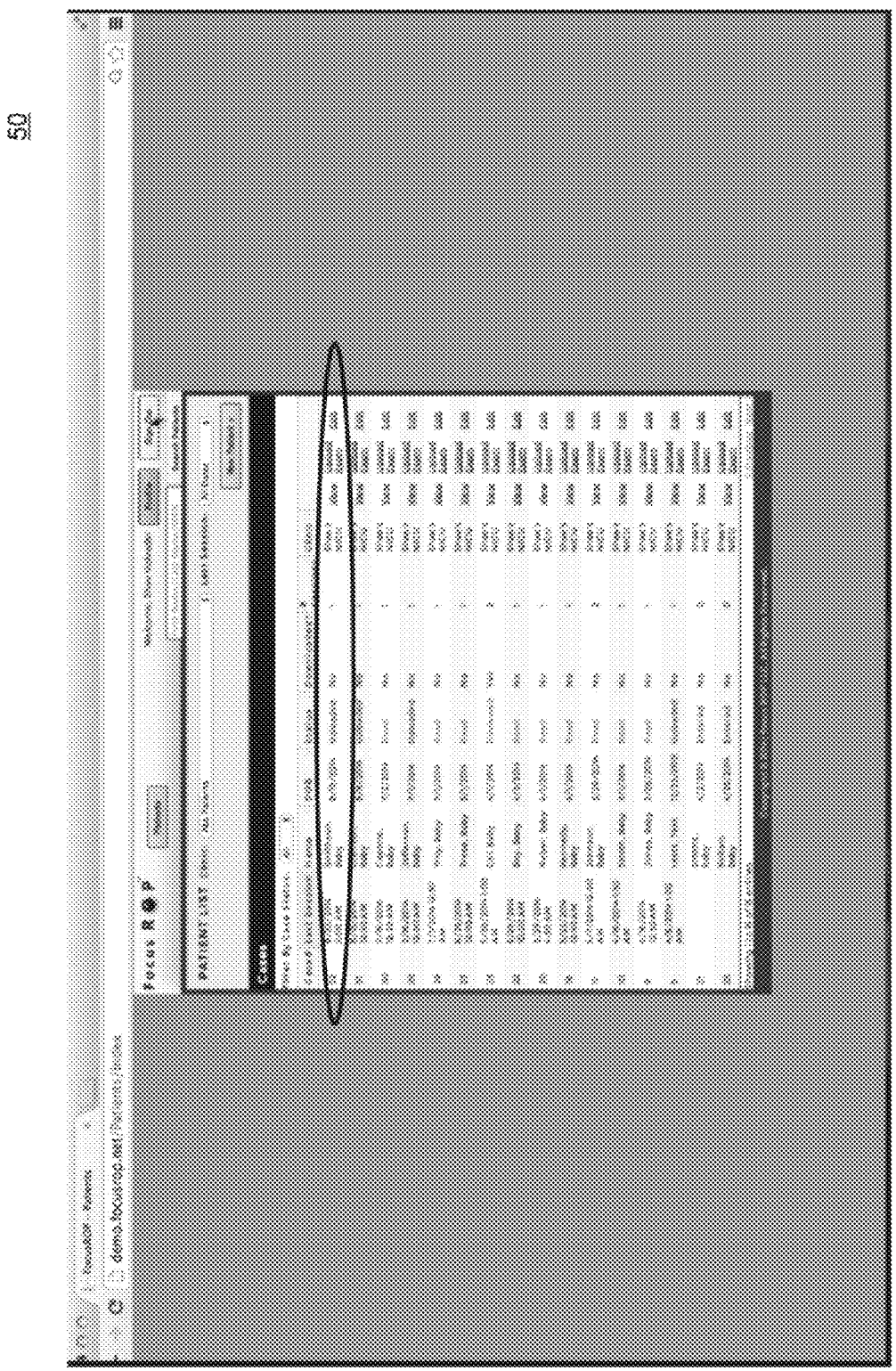
FIGS. 5A-5Z are screen shots for performing analysis and diagnostics on the uploaded patient photo information according to an embodiment of the invention.
Figure 5B:
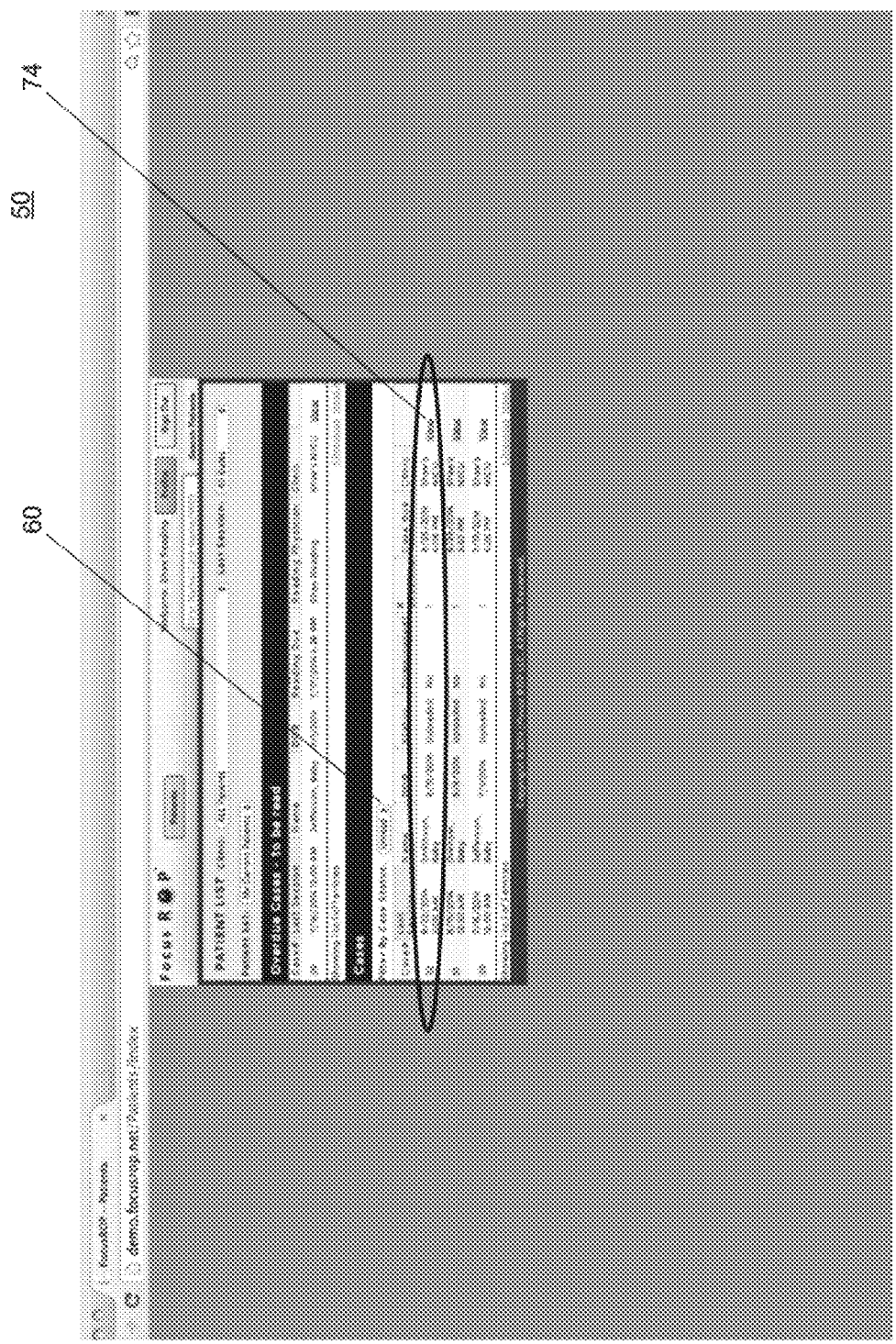
Figure 5C:
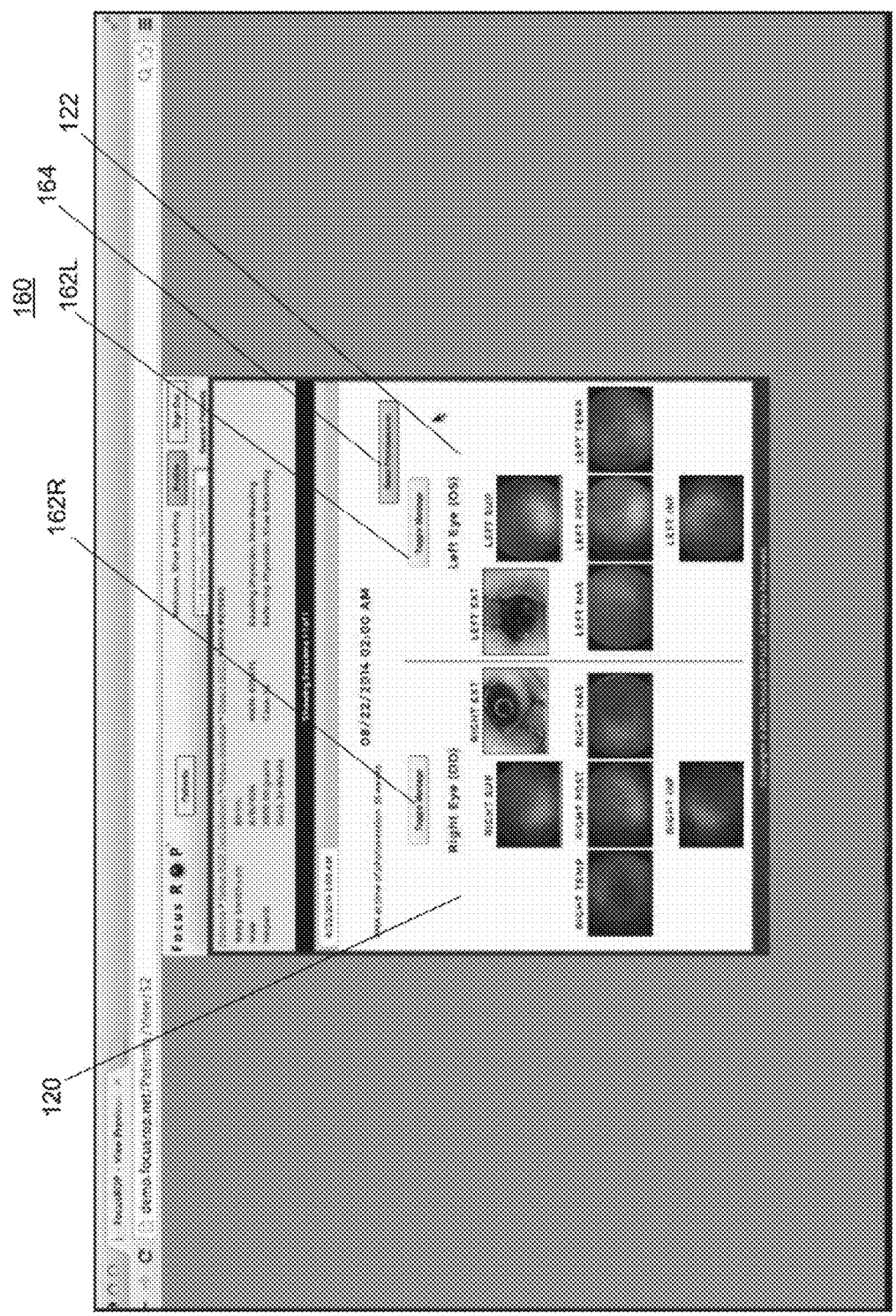
Figure 5D:
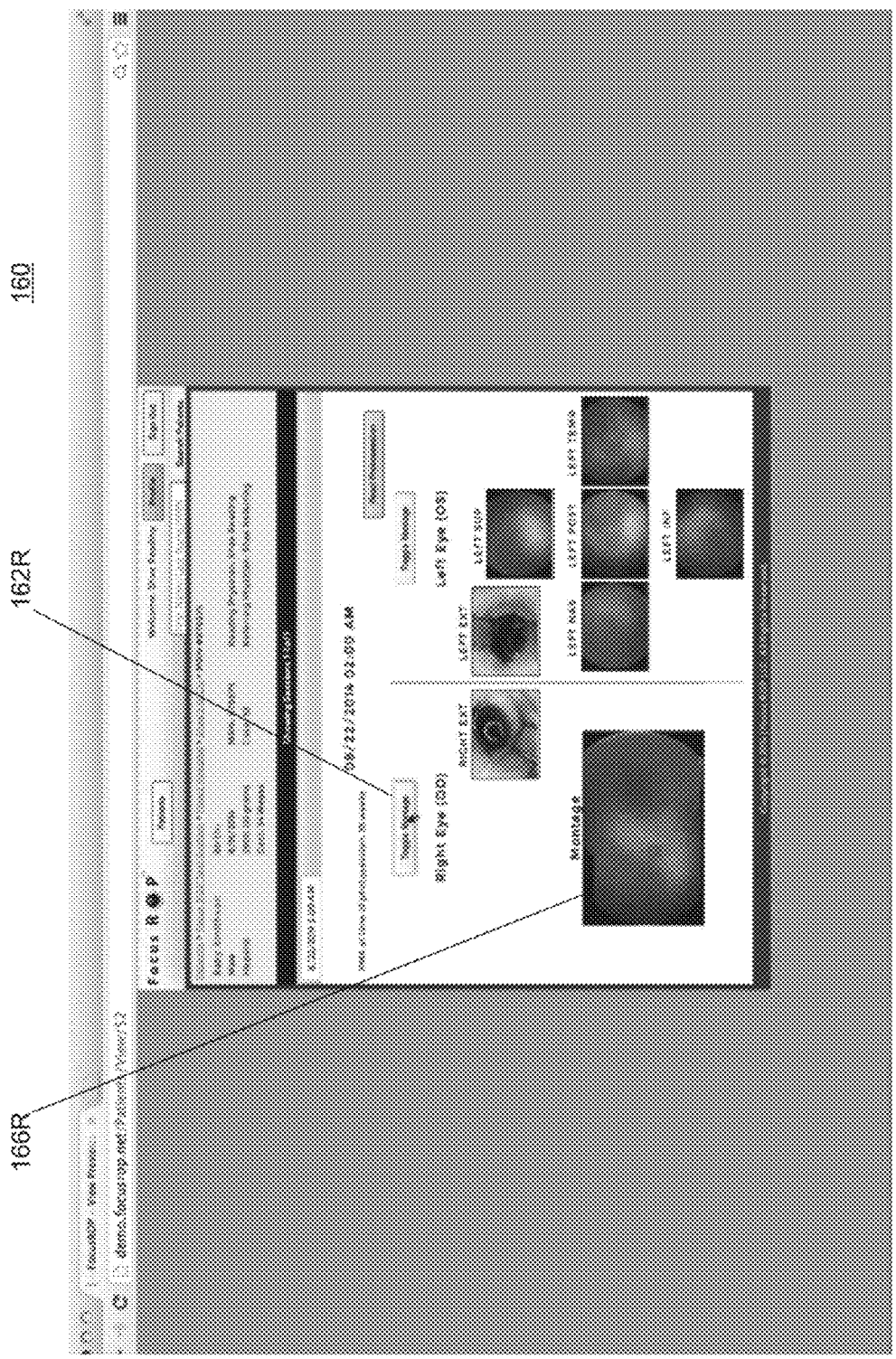
Figure 5E:
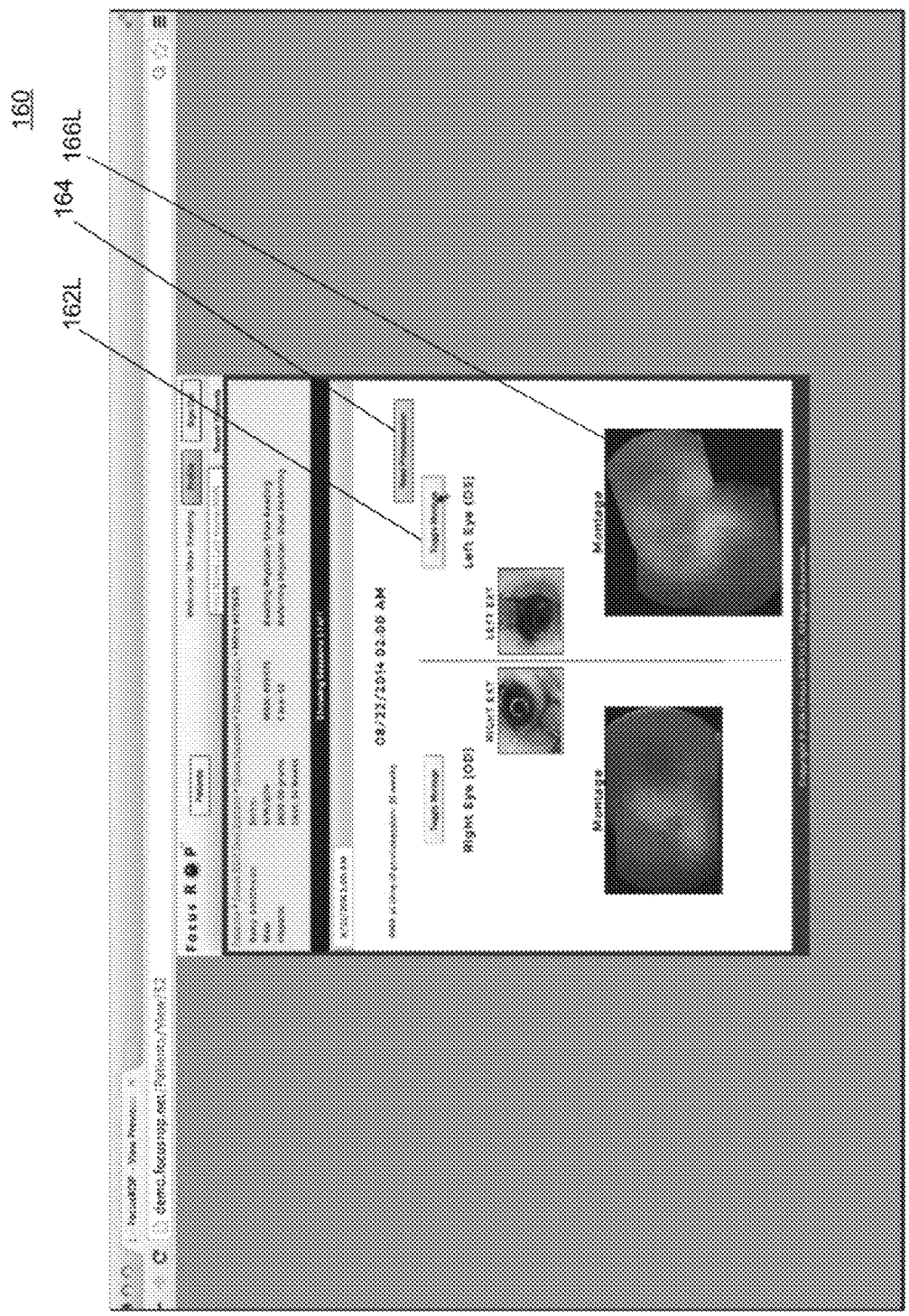

In response to the save and next button 104 being selected, the photo session information screen appears 110, as shown in FIG. 4C, for loading photographs of the retina into the patient file, as step two of three of the new patient upload, with a confirmation message 112 that the patient was successfully added to the database in FIG. 3C. A patient information field 114 appears at the top of the page 110, and fillable fields are provided for the date of when the photos were taken 116 and the time the photos were taken 118. The photo session information screen 110 is split into sections for the right eye (OD) 120 and the left eye (OS) 122. Within each of the sections (120, 122) a template with a series of boxes labeled for the series of views of the photographed eye are provided where a photograph is dragged or dropped. In a specific embodiment the views include right and left eye version of the external, inferior, nasal, posterior, superior, and temporal. As shown in FIGS. 4B-4D an overlay window of the photographs 126 has the file of photographs which are dragged and dropped into the corresponding labeled squares for the right eye (OD) 120 and the left eye (OS) 122. For example in FIG. 4C the photo for the external OO 128 is dragged and dropped into the square for the left ext., and in FIG. 4D the photo for the superior OO 130 is dragged and dropped into the corresponding square on the right eye (OD) 120 side. FIG. 4E shows the completion of the transferring of the photos to the patient file in step 2 of the new patient upload. With the selection of the save and next button 132, the system stores the photos and the user is provided with confirmation page 140 (FIG. 4F) to confirm the information (step 3 of 3). Furthermore, the user is informed that they must confirm the photo session in order to send the file to the reading physician for review 142. Selection of the "confirm and send to reading physician" button 144 completes the patient upload process. The Exam upload confirmation page 150 (FIG. 4H) notifies the user that the upload was successful 152, and acknowledgement by the user by pressing the return to patient list 154 sends the user back to the patient list as shown in FIG. 5A. The patient list 50 in FIG. 5A is filtered 60 by unread cases in FIG. 5B, and the newly added patient "Smithson Baby" of FIG. 3C and FIGS. 4A-4H is circled (for illustration only) in both FIGS. 5A and 5B. Selection of the view link 74 initiates patient information screen 160 in FIG. 5C with the patient's biographical information and uploaded examination photographs separated in accordance to the right eye 120 and left eye 122. Selection of the toggle montage button 162R in FIG. 5D provides the user with a montage 166R of the right eye formed with the individual examination images for the right eye. FIG. 5E shows the selection of the toggle montage button 162L which provides the user with a montage 166L of the left eye formed with the individual examination images for the left eye. Selection of the read presentation button 164 initiates the reading process of the uploaded patient eye examination images which begins in FIG. 5F with read photo session screen 170.

Figure 5F:
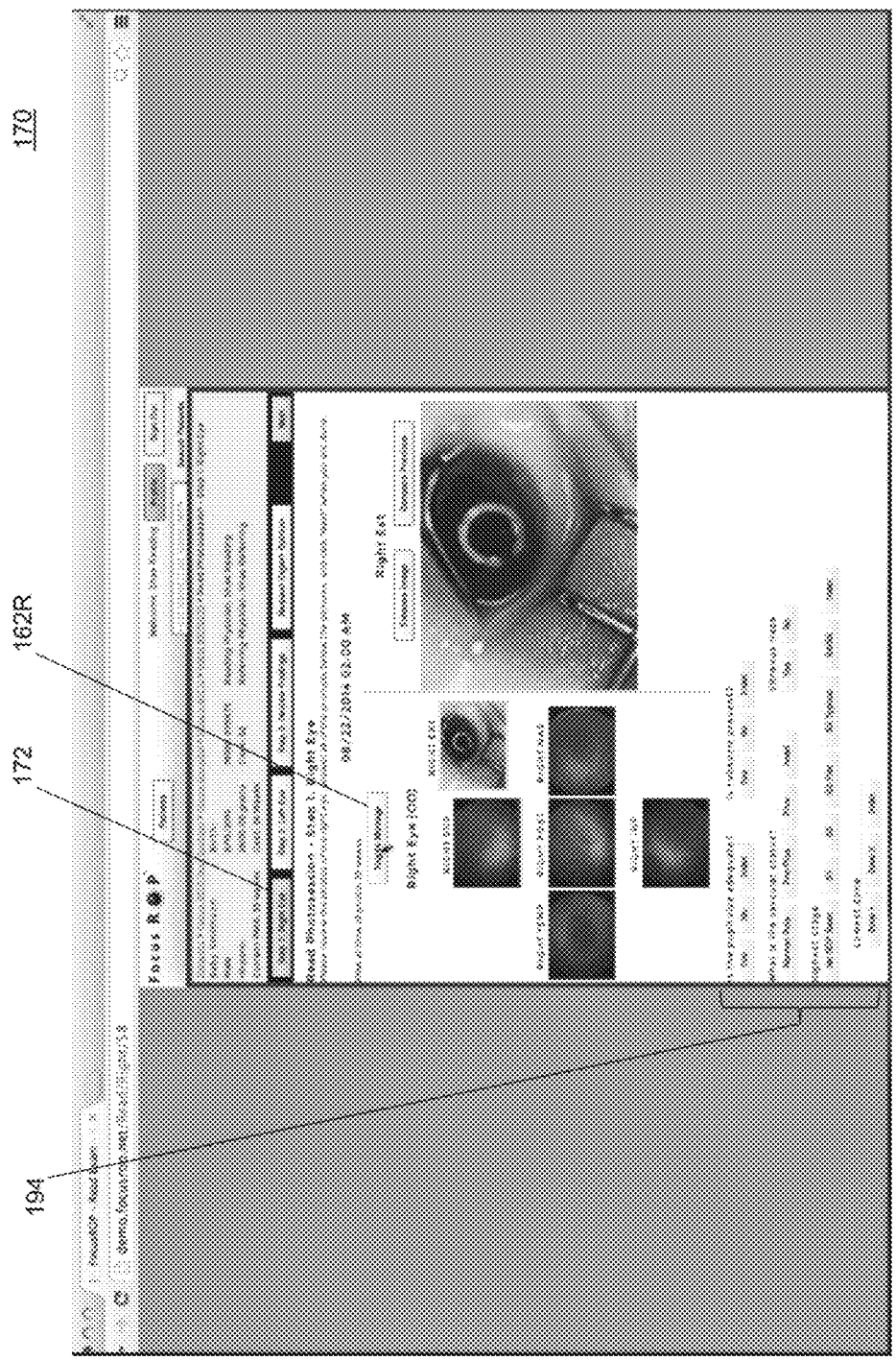
Figure 5G:
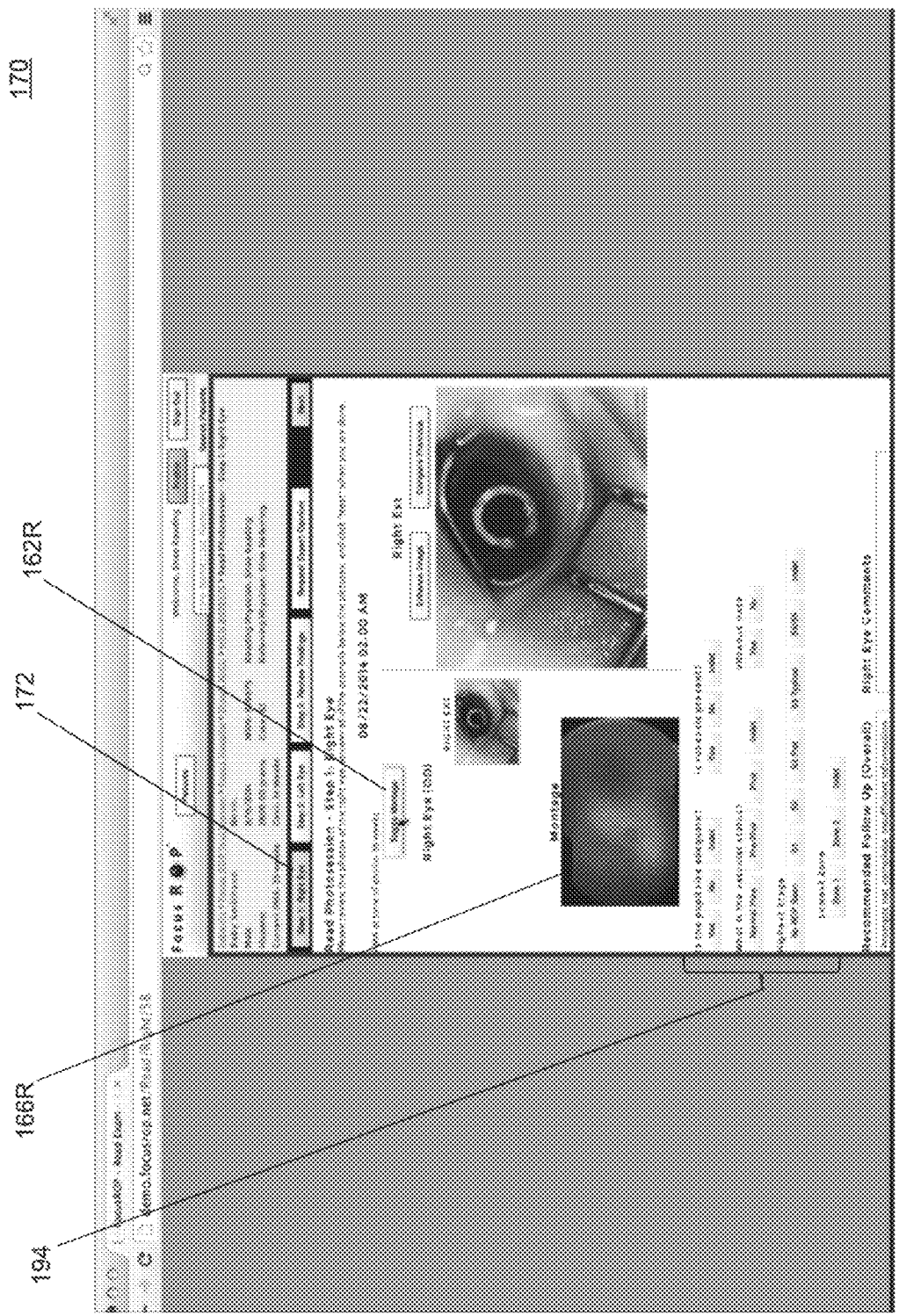
Figure 5H:
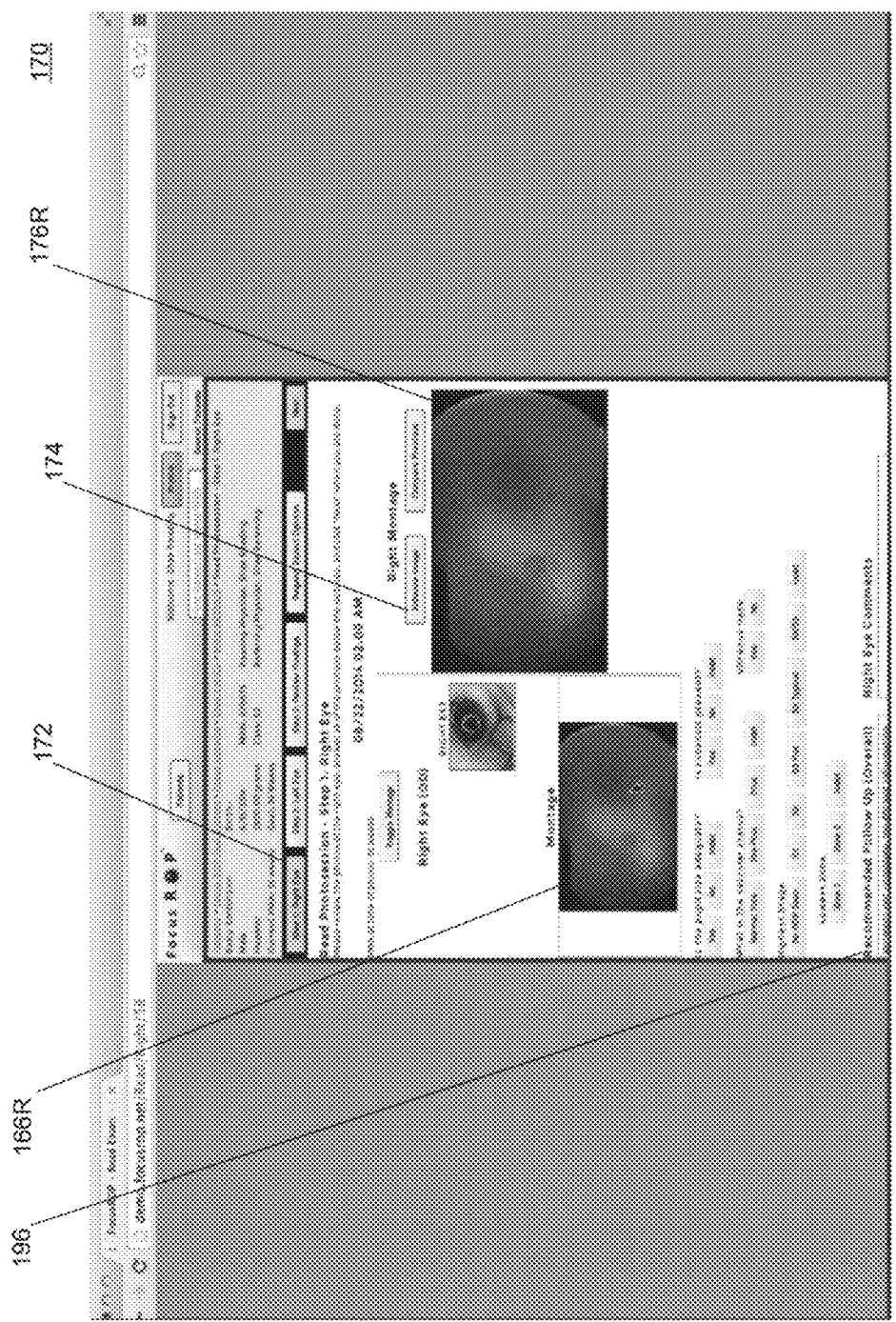
Figure 5I:
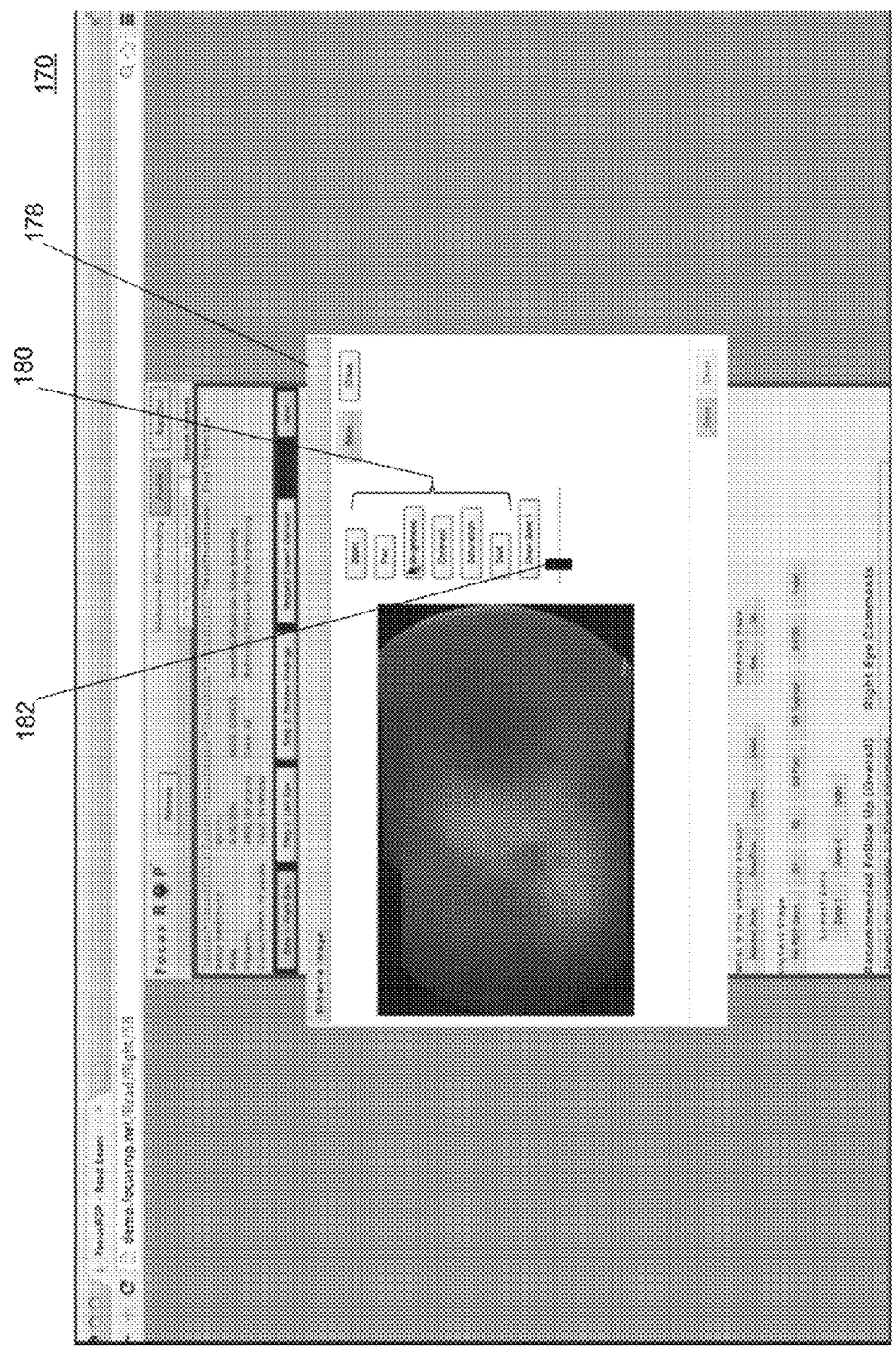
Figure 5J:
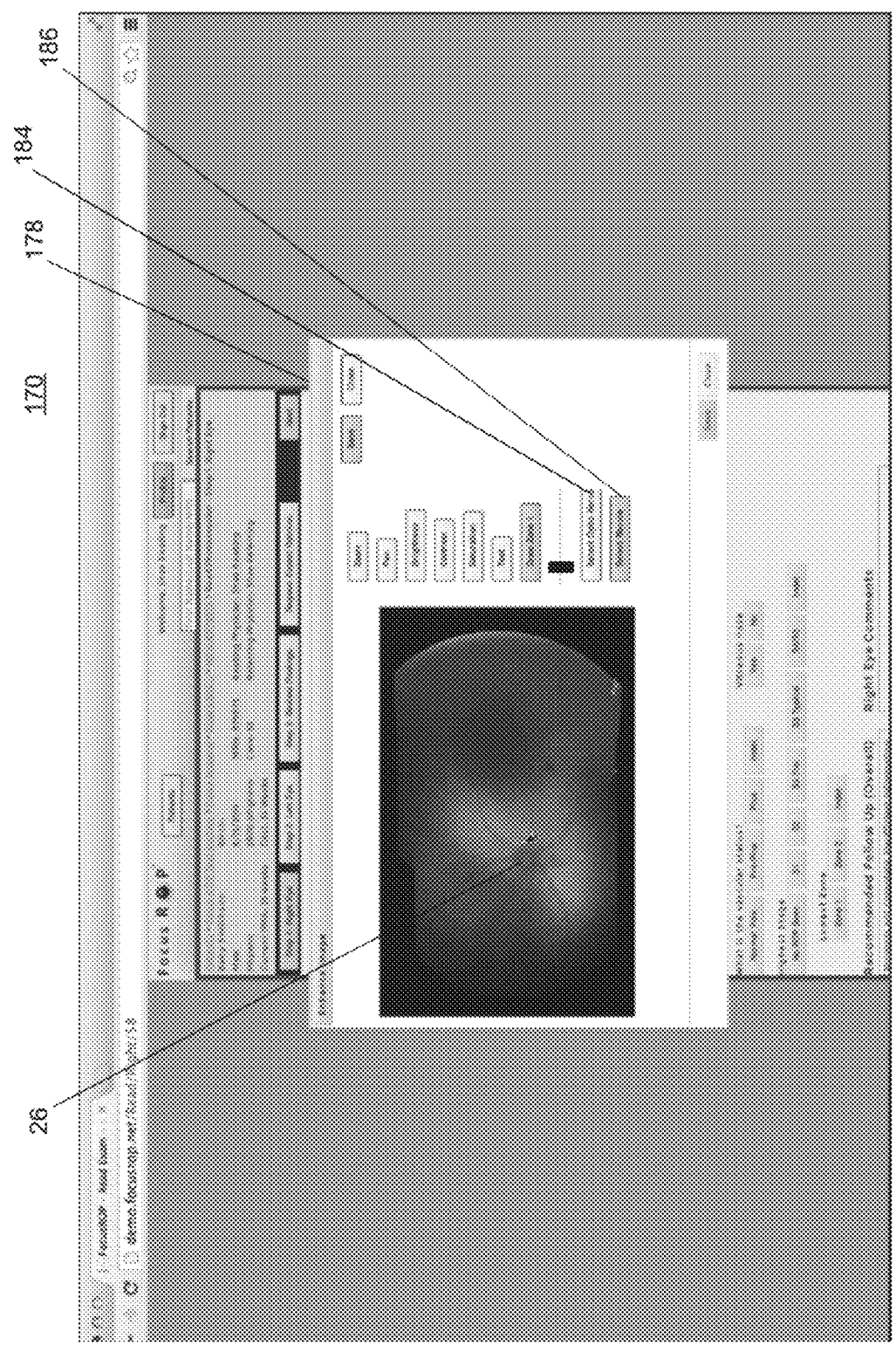
Figure 5K:
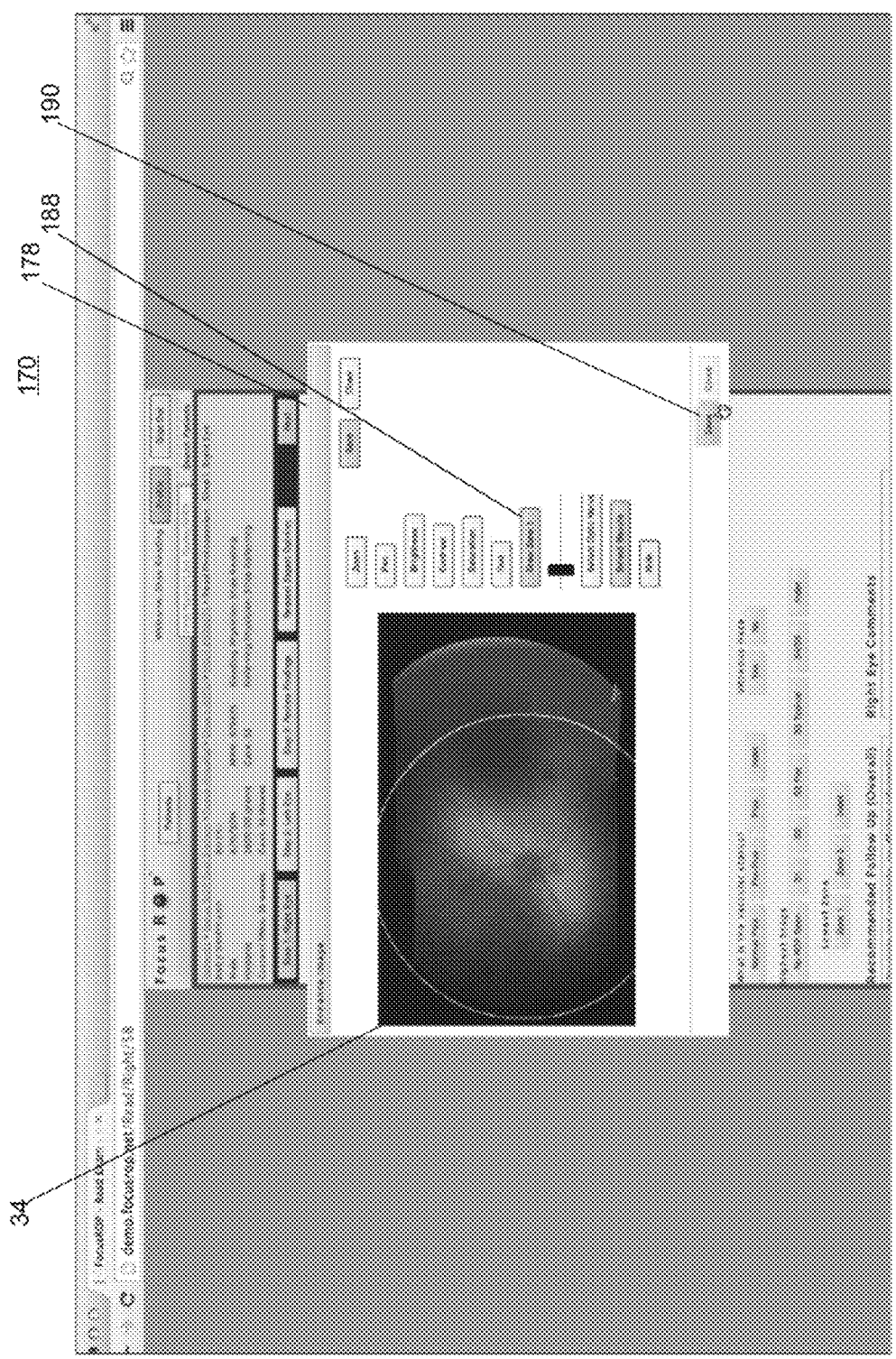
Figure 5L:
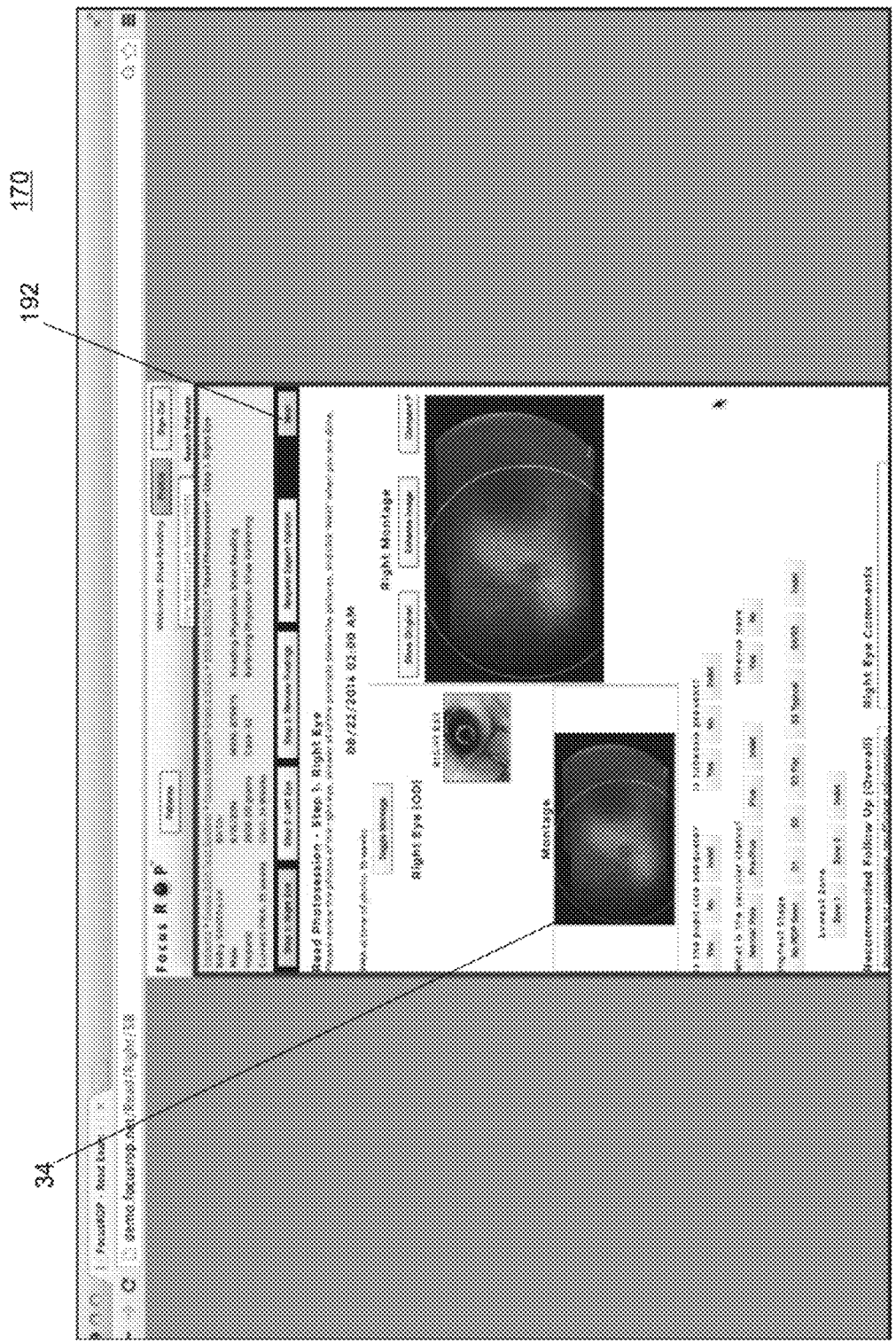
Figure 5M:
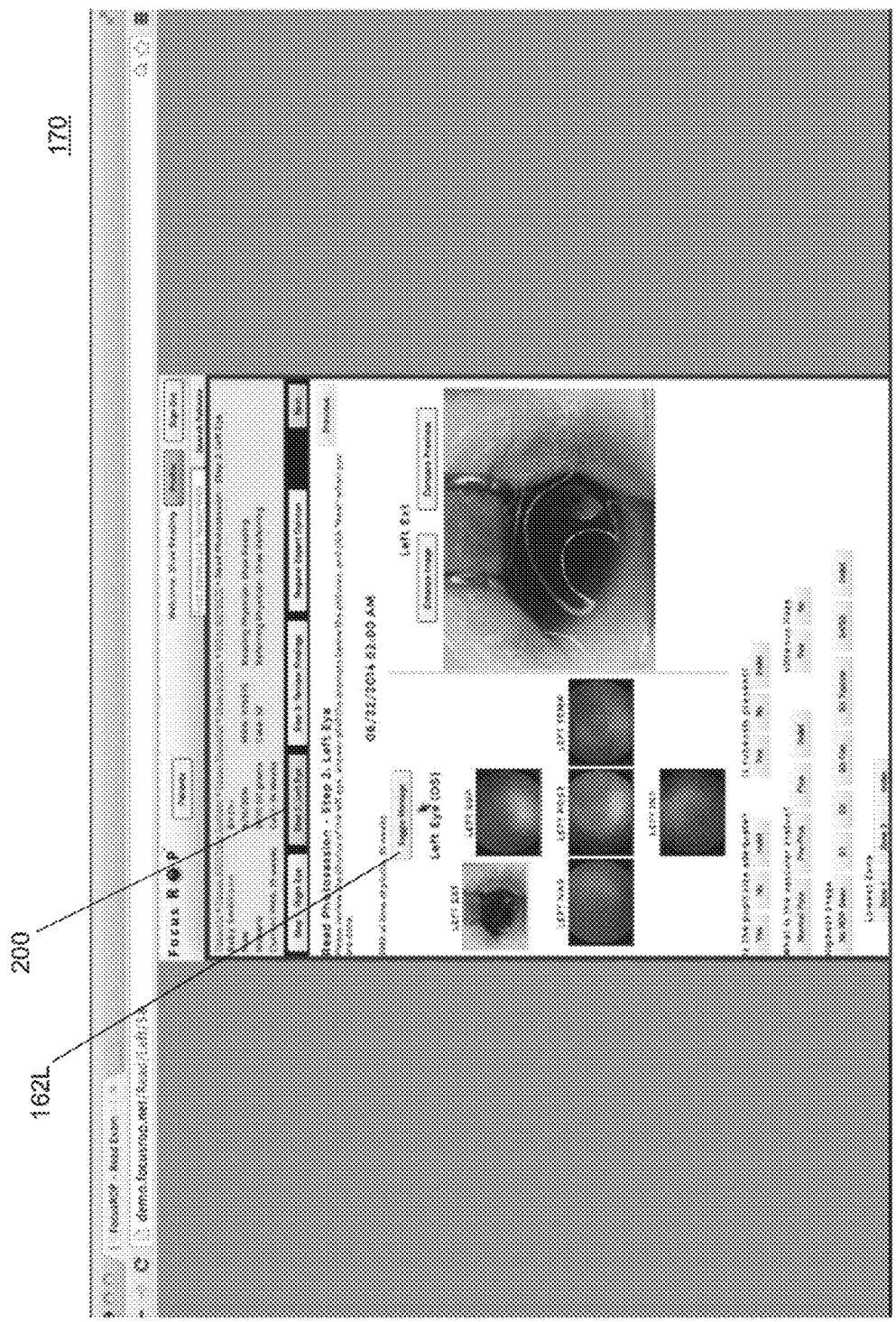
Figure 5N:
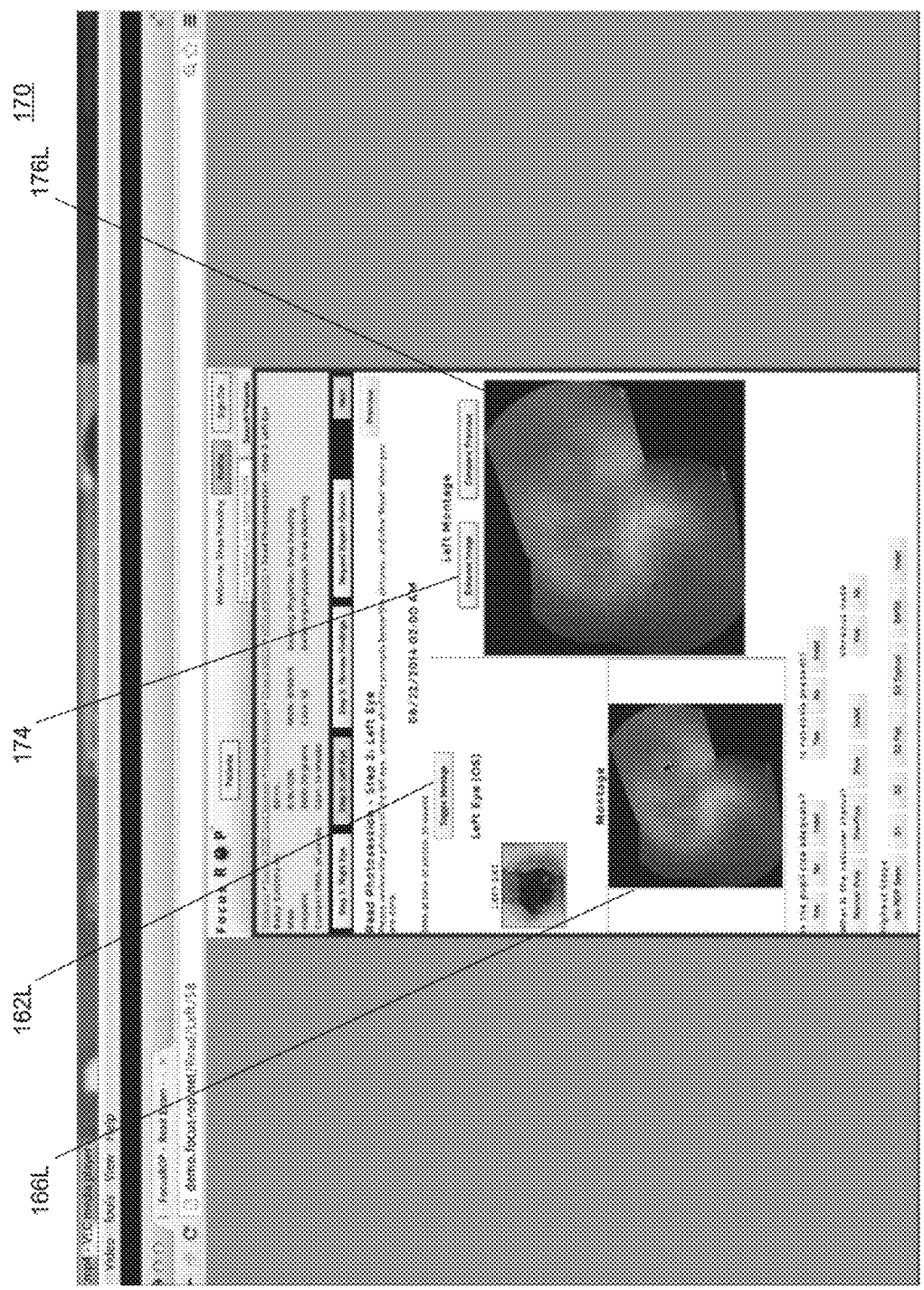
Figure 50:
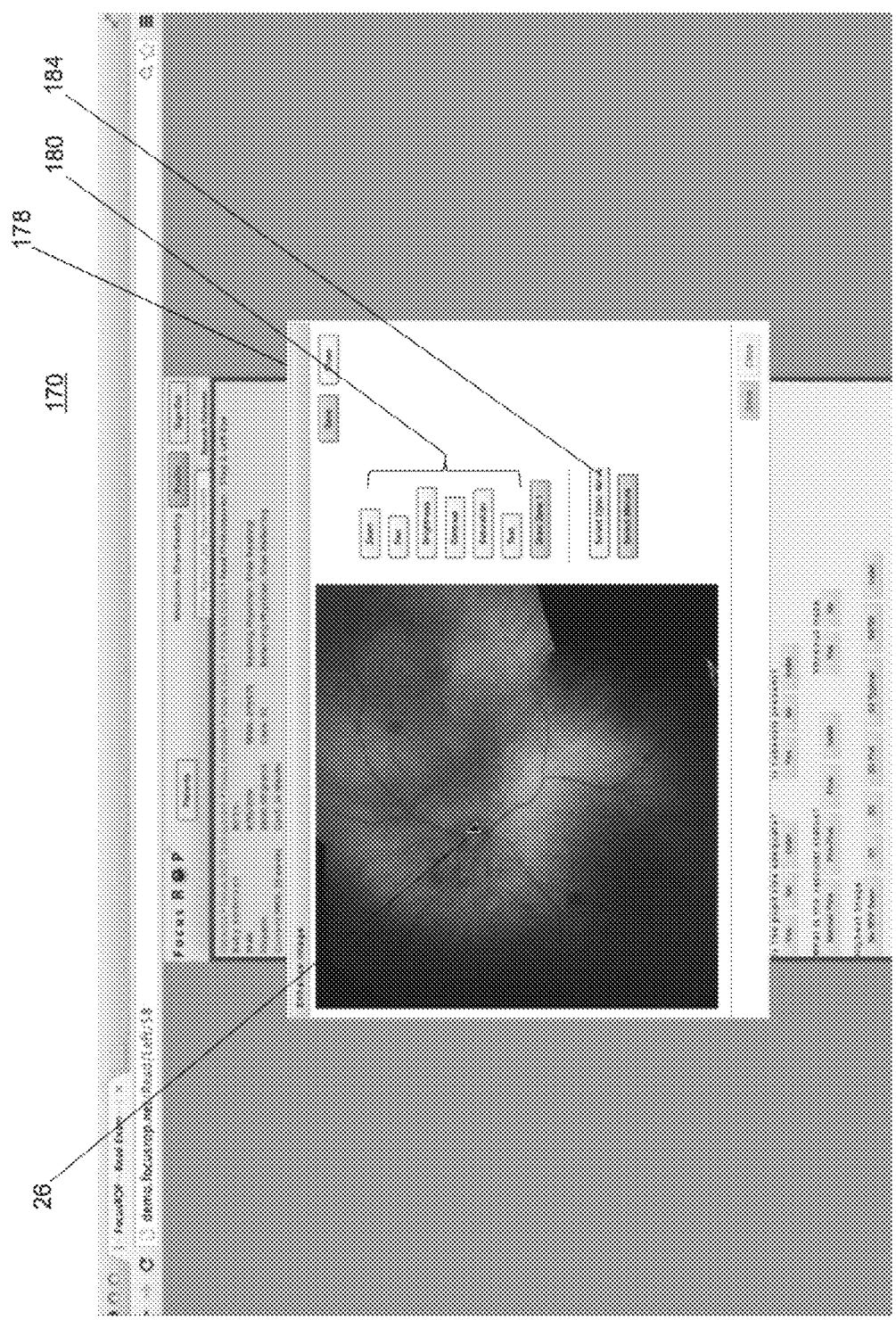
Figure 5P:
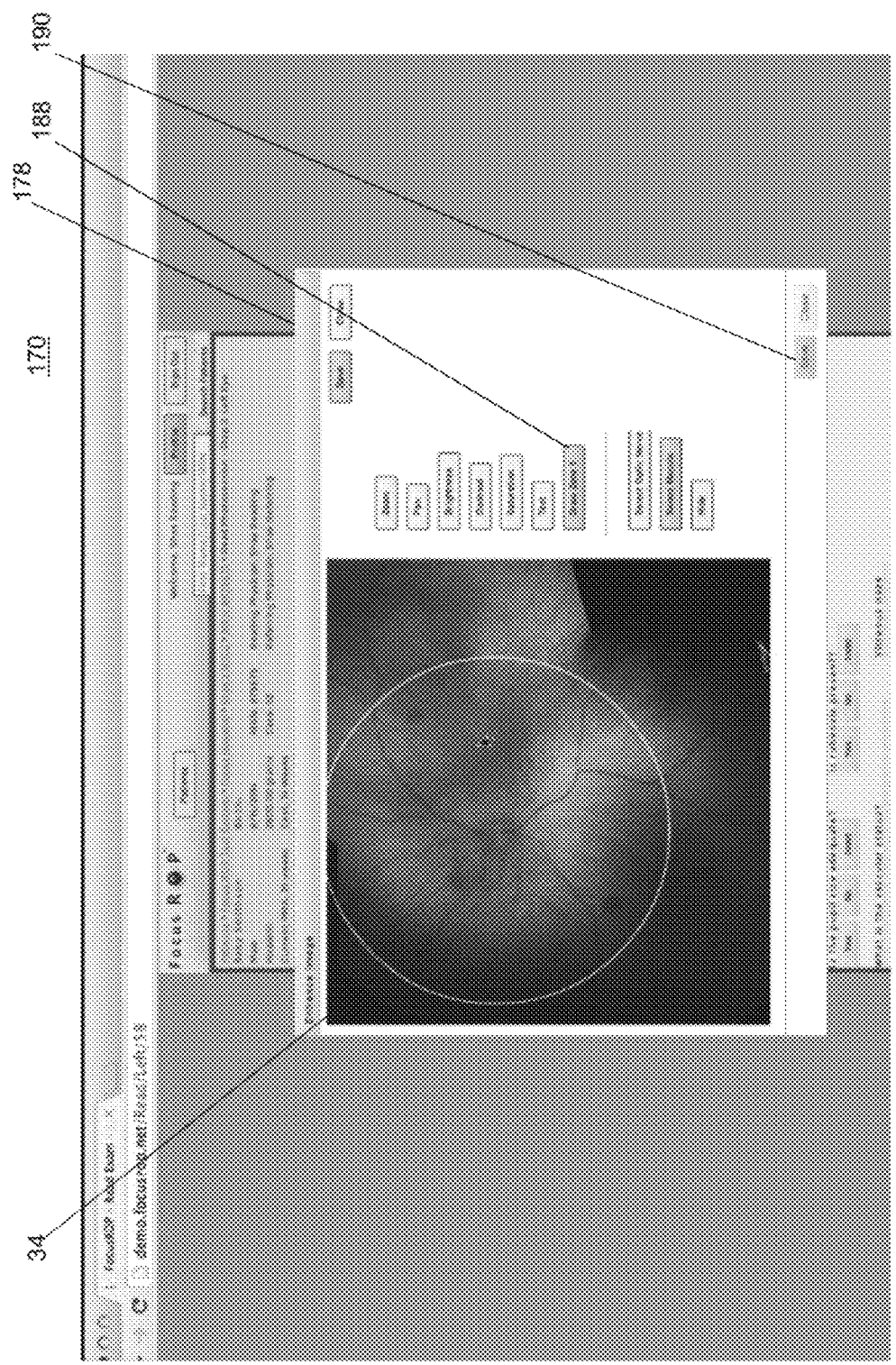
Figure 5Q:
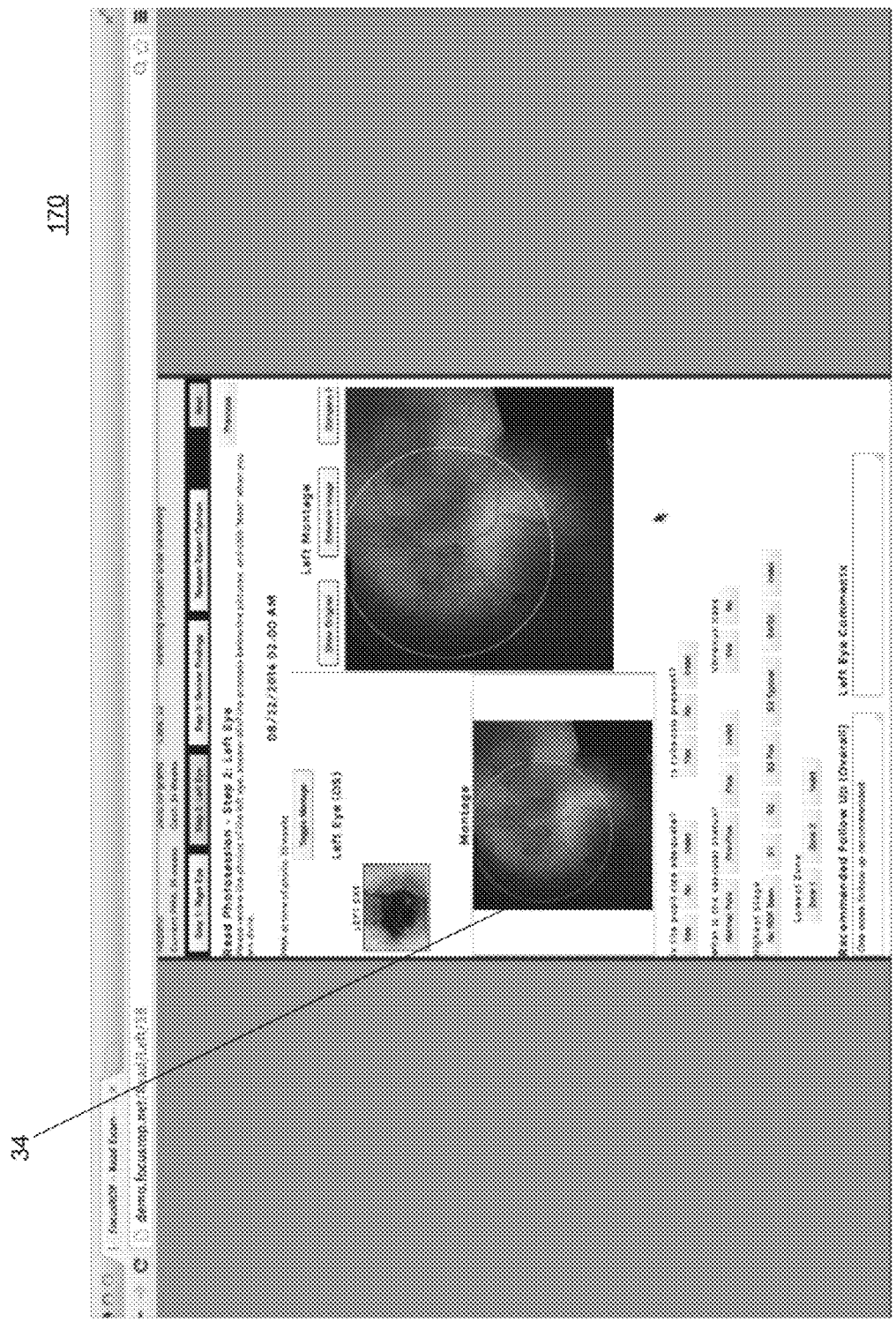

As shown in the non-limiting example of FIGS. 5F and 5G, the reading process begins with the right eye (step 1) 172, however the physician may also configure the system to begin with the left eye. The toggle montage button 162R provides the user with a montage 166R of the right eye formed with the individual examination images for the right eye. Clicking or selecting the montage 166R, enlarges the picture 176R. Questions 196 presented to the physician during the read photo session include: Is the pupil size adequate; Is rubeosis present; What is the vascular status; Is there virtuous haze; Highest stage; Lowest zone, etc. Selecting the enhance image button 174 initiates the pop up overlay 178 as shown in FIGS. 5I-5K. Enhancement buttons 180 provide the user with the ability to pan or zoom in/out the selected image, as well as adjust image parameters such as brightness, contrast, and saturation. In addition, the text button provides the ability to add overlay text to the image. Slider control 182 may be used to adjust the image parameters. As shown in FIGS. 5J and 5K, the selection of the draw zone 1 button 188 begins with identification of the optic nerve 26 with select optic nerve button 184, and the select macula button 186. Following the selection of the optic nerve 26 and macula 24, the system automatically draws the circle 34 that represents zone 1, which is used in the diagnosis and treatment of ROP. The operator designates the position of the optic nerve; and then the system may automatically draws the boundary of zone 1. The save button 190 saves the changes made to the image. Selection of the next button 192 initiates step 2 of the read photo session for the left eye as shown in FIGS. 5M-5R. The available analysis options and screens are identical to those described for the right eye and are not repeated.

Figure 5R:
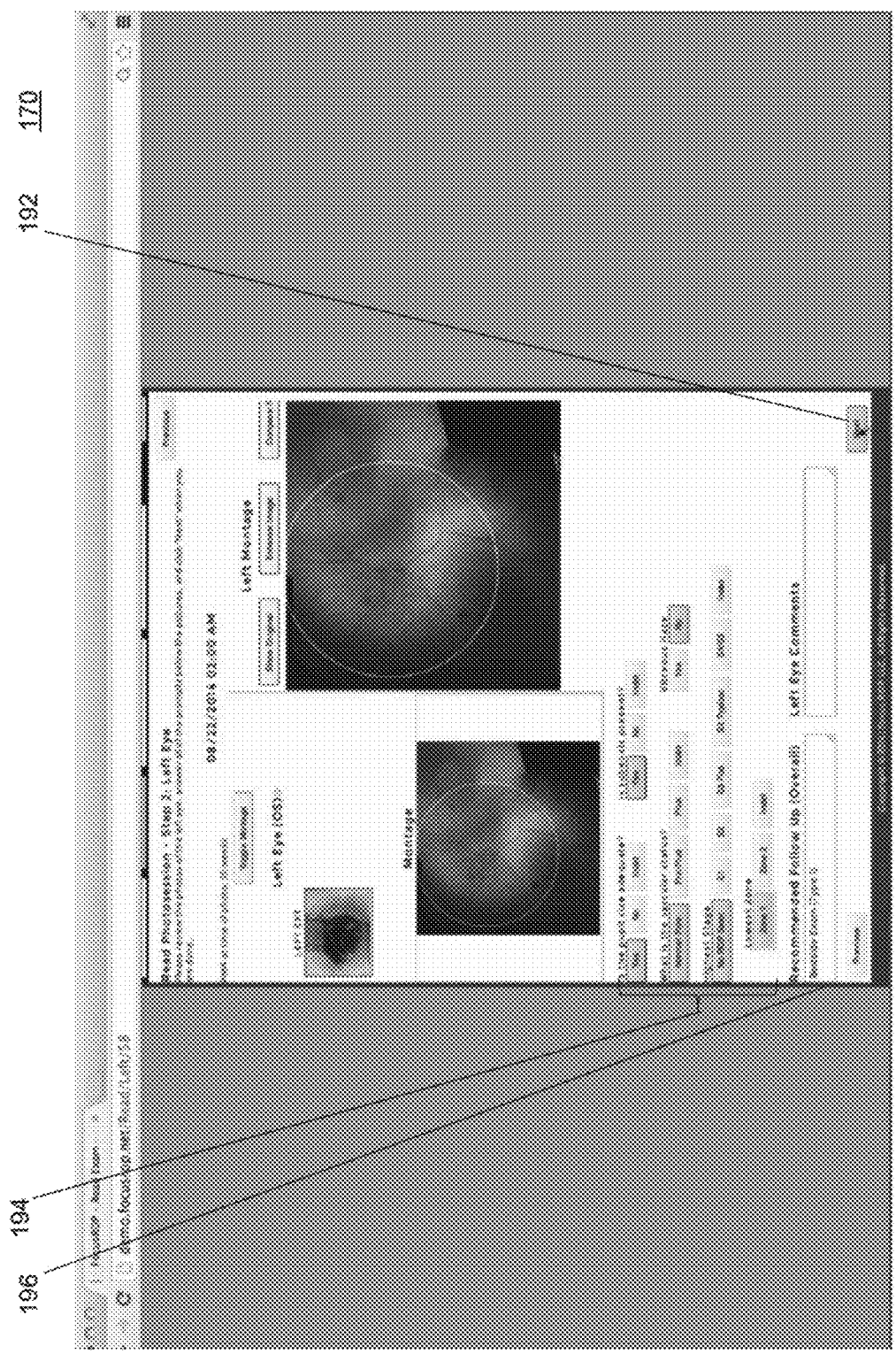
Figure 5S:
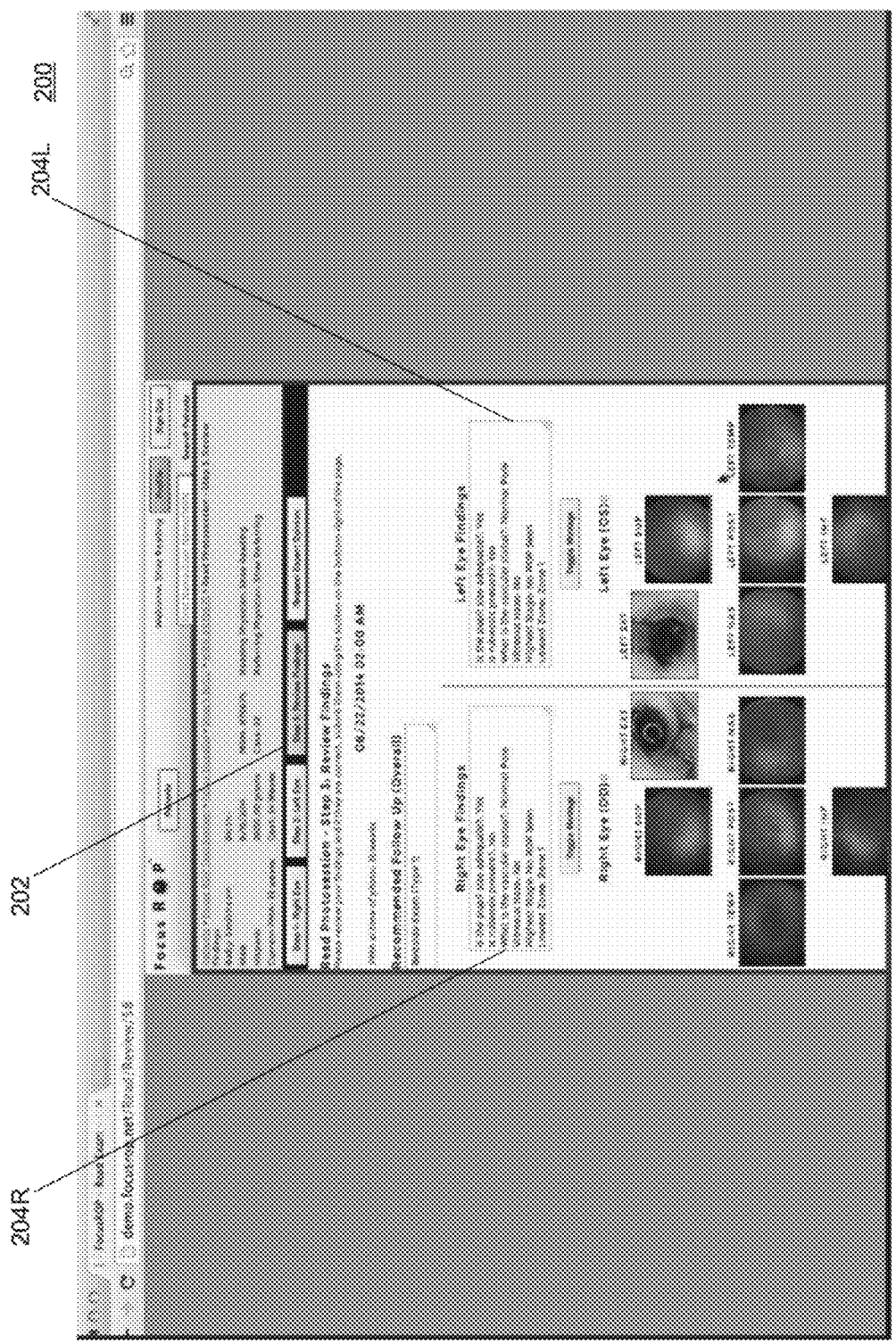
Figure 5T:
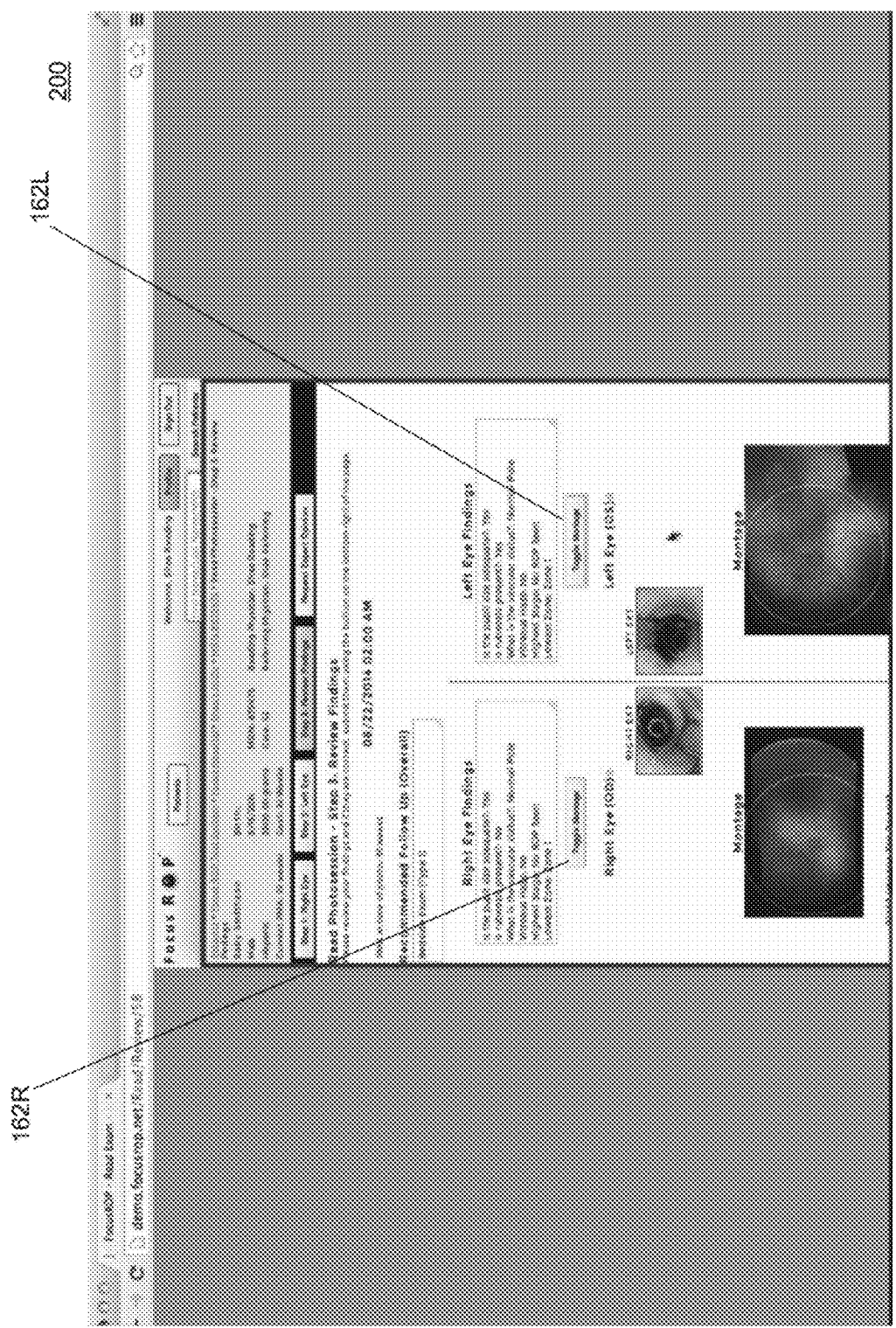
Figure 5U:
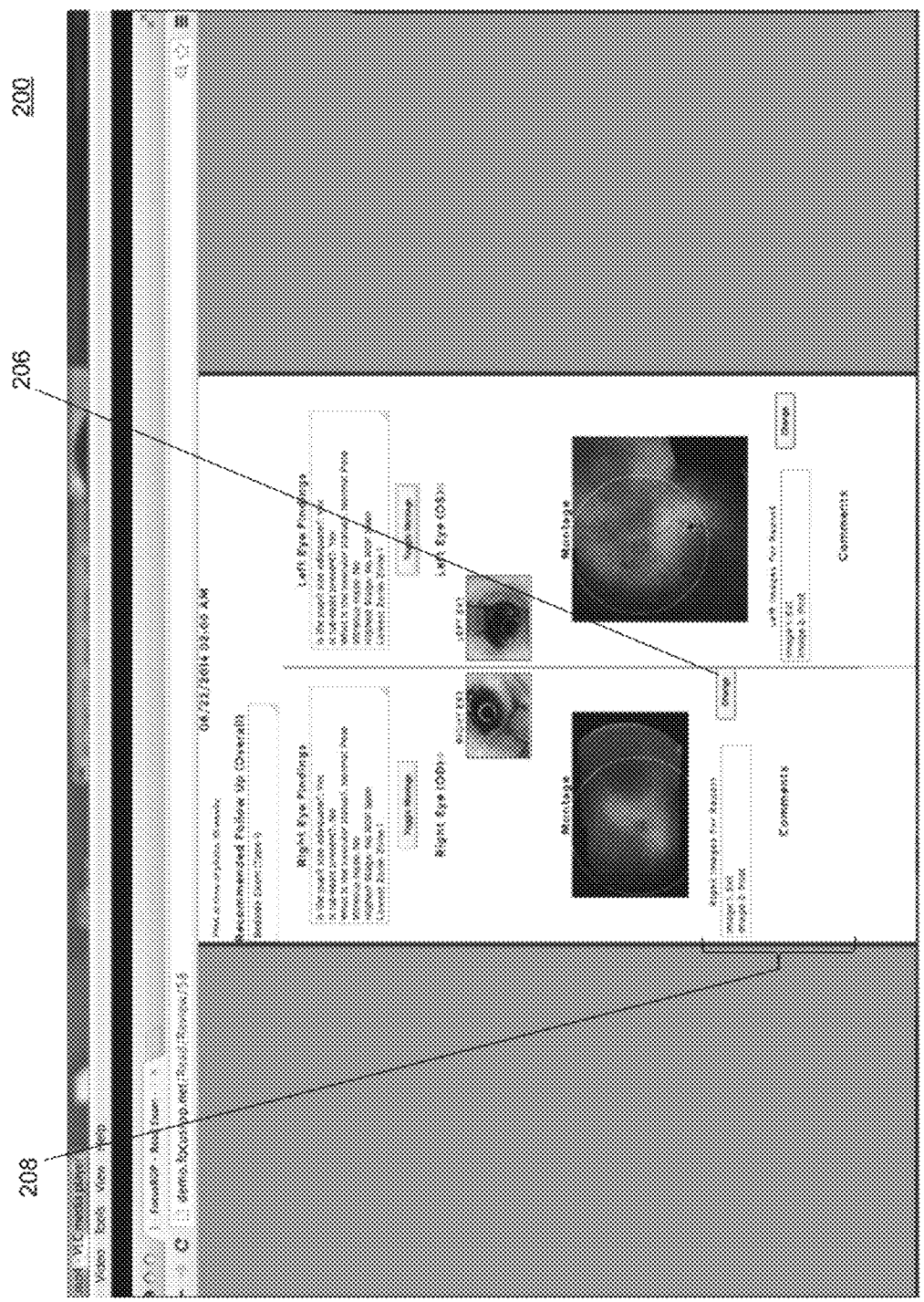
Figure 5V:
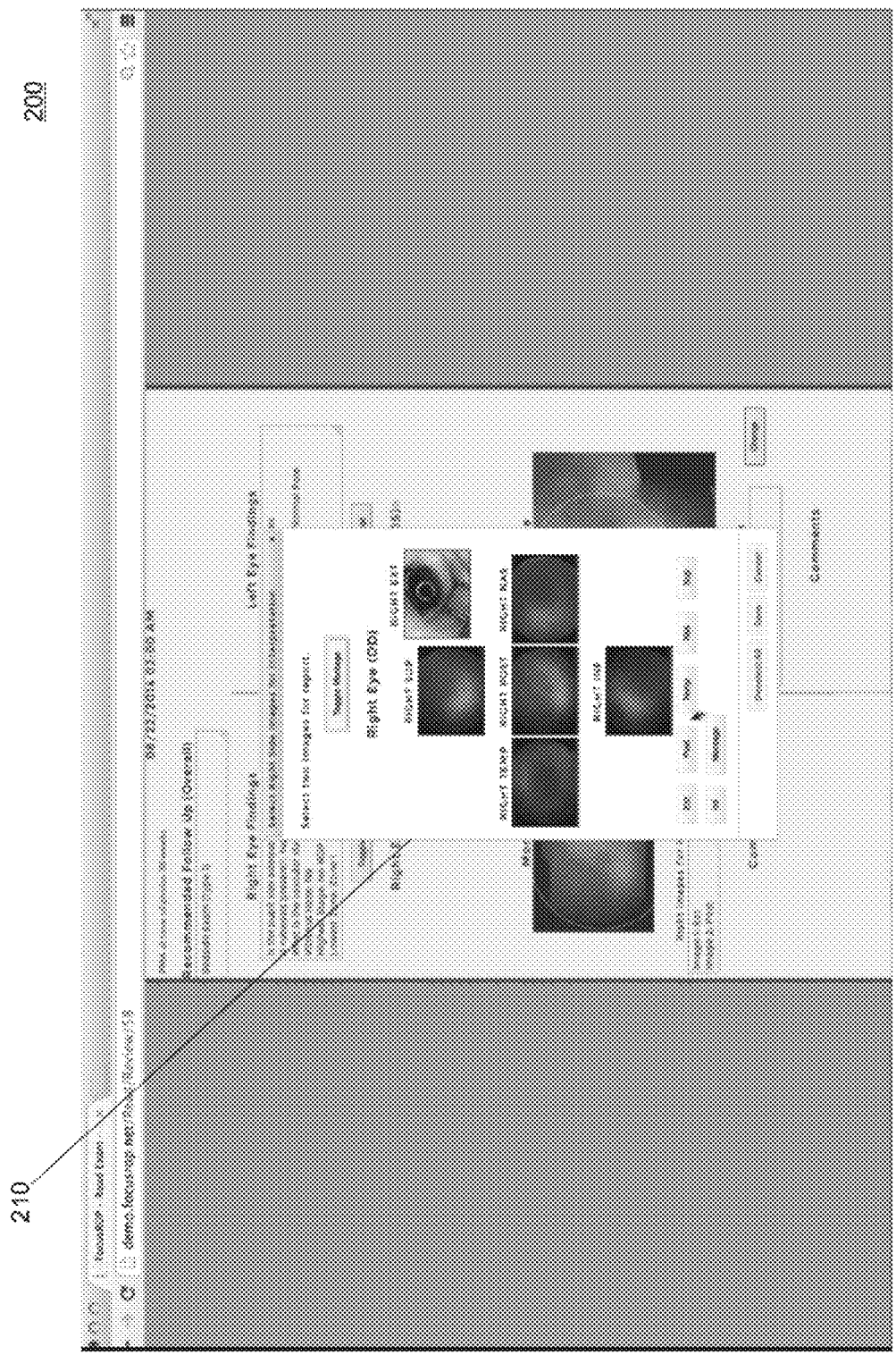
Figure 5W:
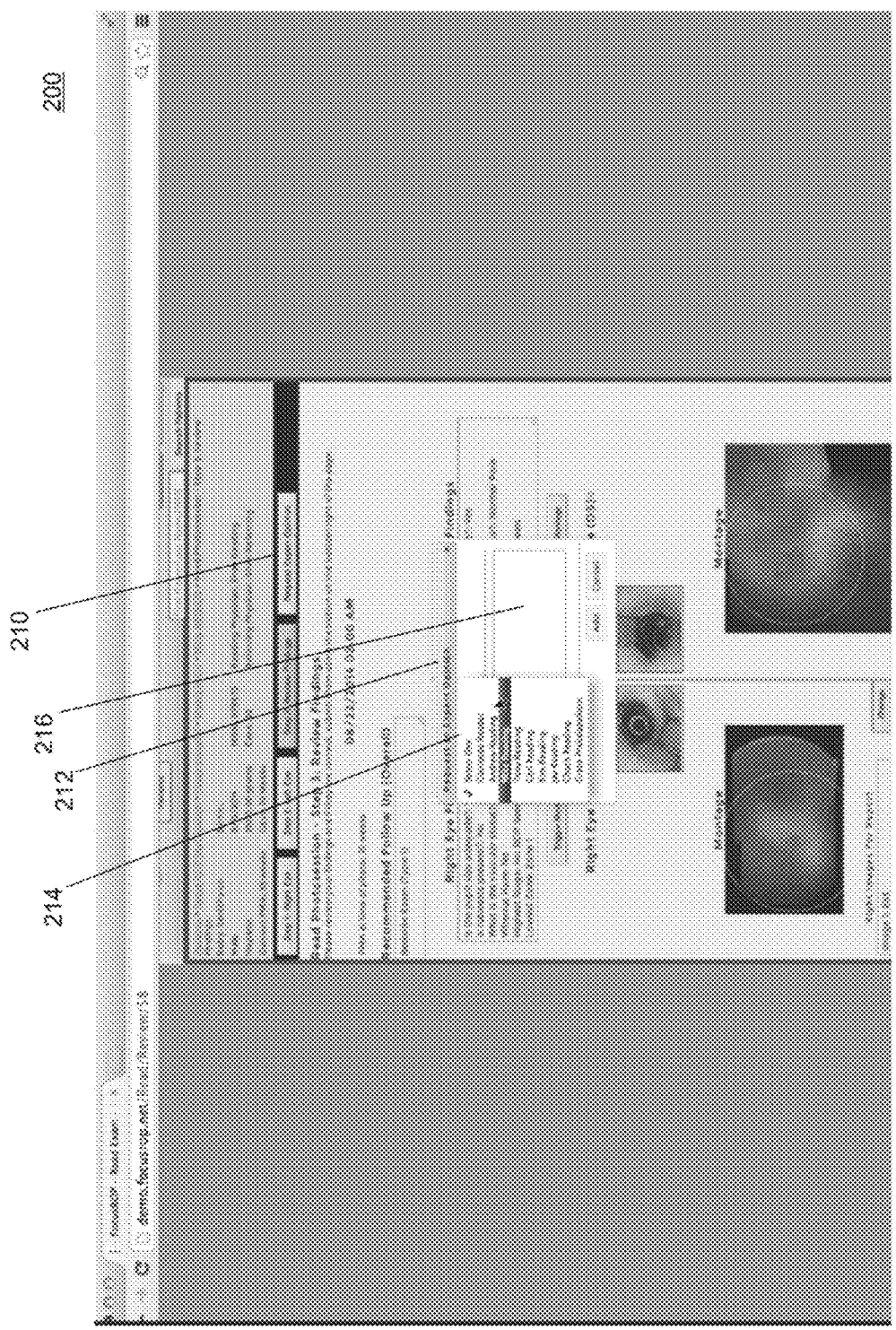
Figure 5X:
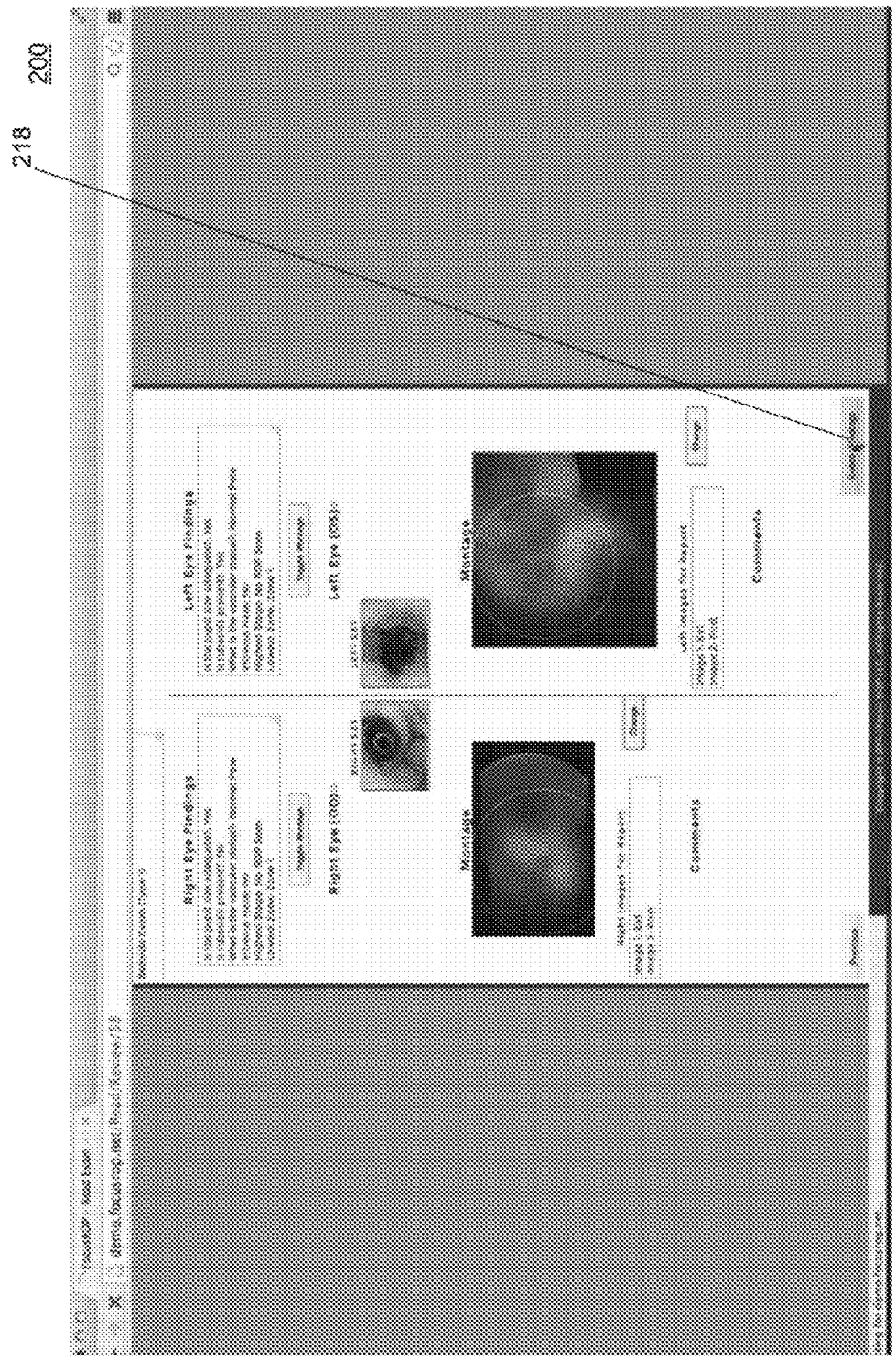

In response to the selection of the next button 192 in FIG. 5R, the read session review screen 200 is displayed as indicated by step 3: review finding indicator 202 as shown in FIGS. 5S-5X. Screen 200 instructs the physician to review their findings with respect to their analysis of the patients exam photos, and if the findings are believed to be correct, the physician is instructed to submit the findings by selecting the submit findings button 218 (FIG. 5X). The answers to questions 194 are summarized in right eye findings 204R and left eye findings 204L. Montage toggle buttons (162R, 162L) are provided to view the images. Comment area 208 is provided for viewer notes for the patient file. As shown in FIG. 5U, the physician may change the images in the report with the change button 206, which in response to the selection of the change button 206 an image change overlay 210 with images appears for the right or left eye as shown in FIG. 5V.

A user or physician may request an expert opinion with button 210 (FIG. 5W). In response to the expert opinion request an overlay 212 appears with a pull down menu 214 of available physicians and a question or comment area 216.

Figure 5Y:
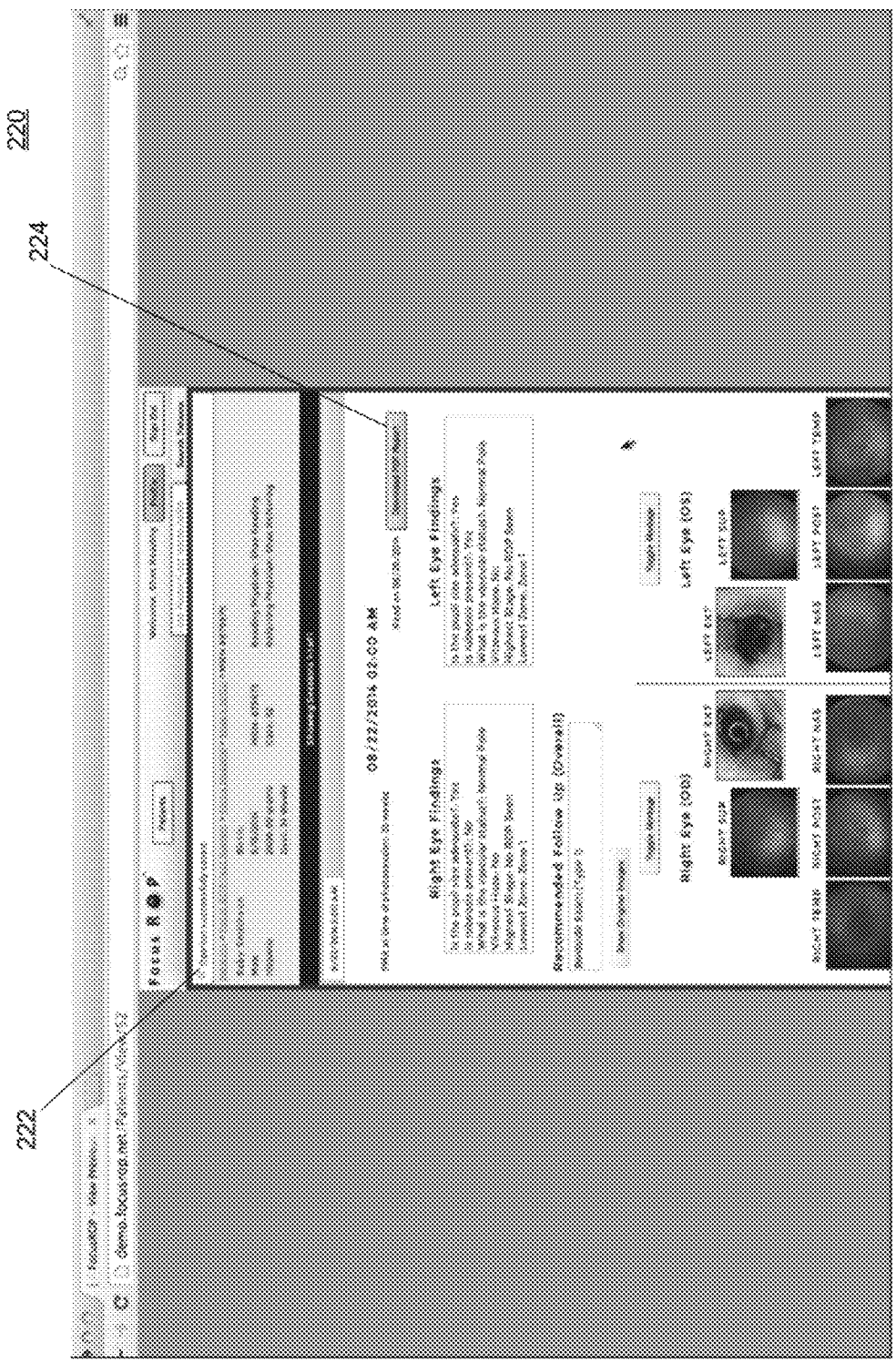
Figure 5Z:
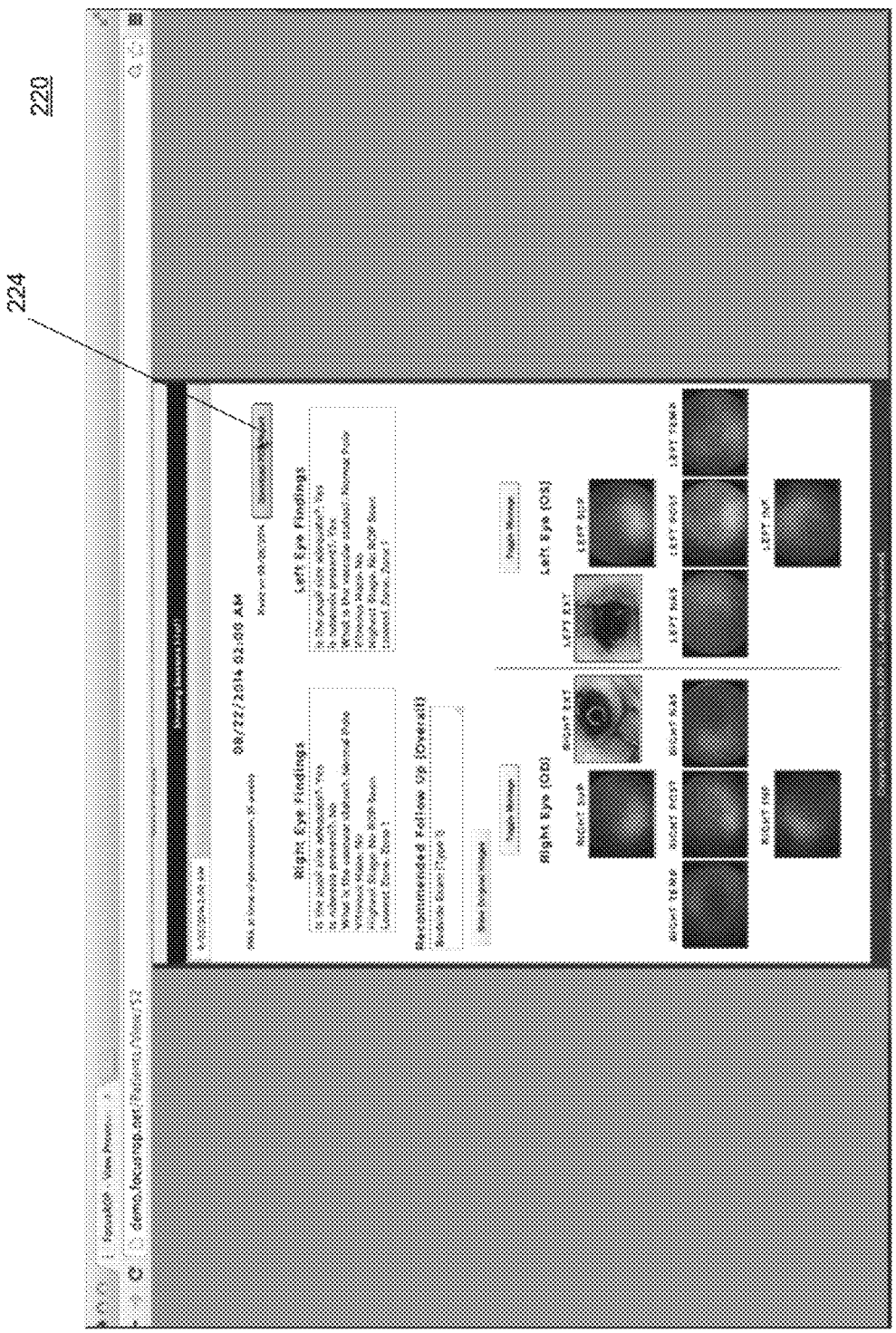
Figure 6:
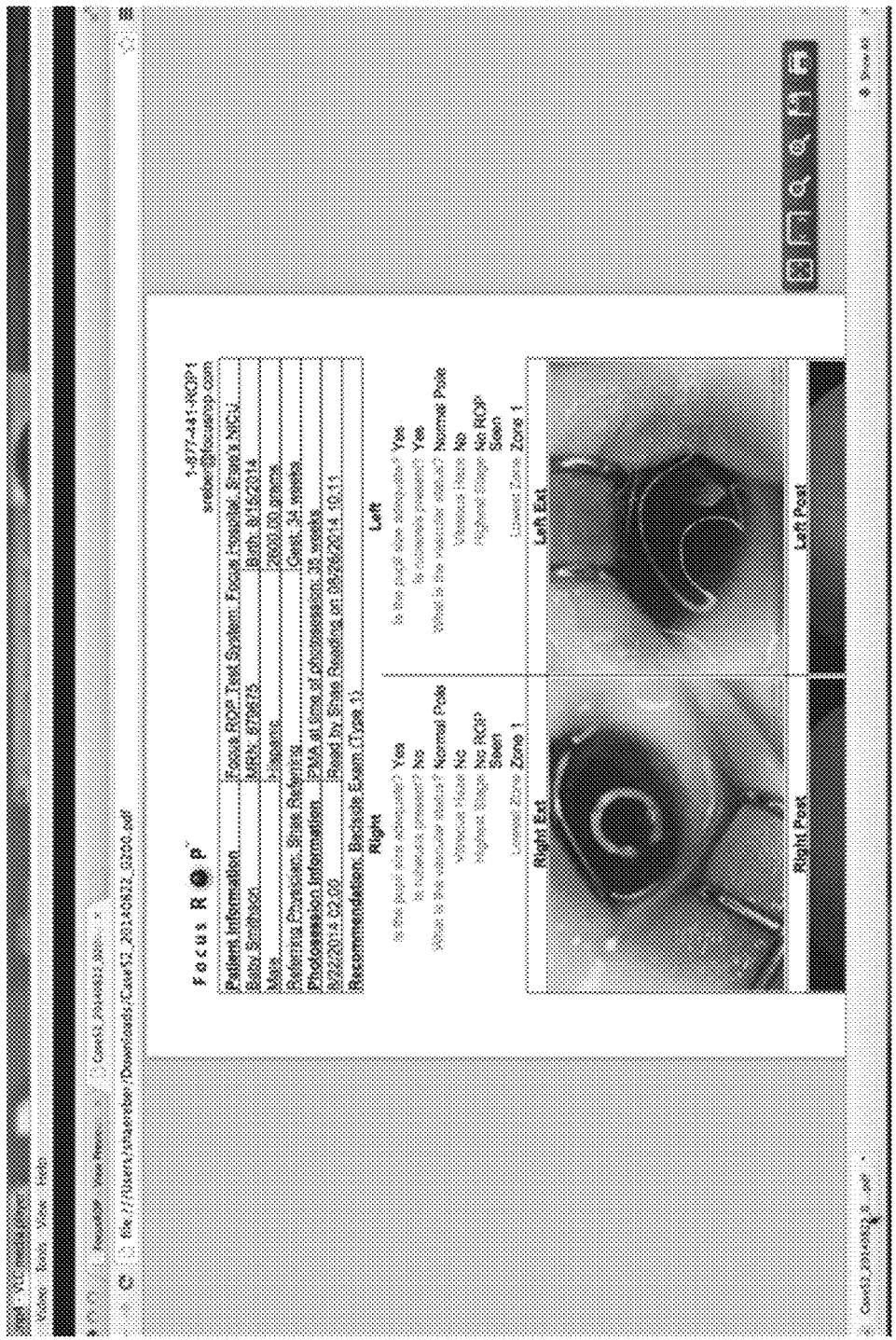
FIG. 6 illustrates a formatted report on a patient's condition based on the analysis and diagnostics of FIGS. 5A-5Z according to embodiments of the invention.

Following the successful submission of findings (opinion) of the reading as indicated by message 222 shown in screen 220 in FIG. 5Y. A report of the finding of the patient exam may be generated with the report request button 224. An example report is shown in FIG. 6.

Figure 7A:
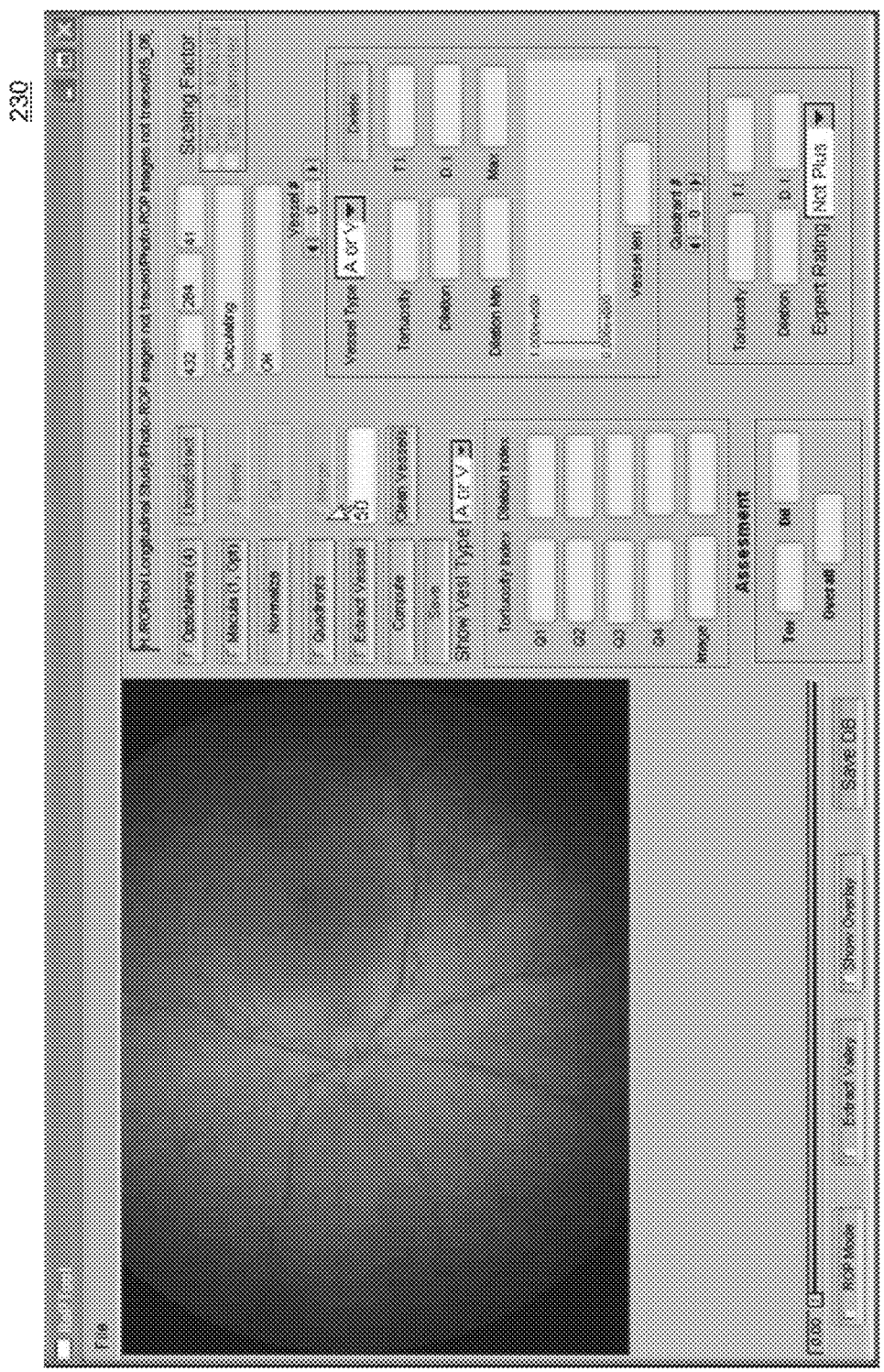
FIGS. 7A-7G are screen shots of an analysis tool for performing automated analysis and diagnostics on the uploaded patient photo information according to an embodiment of the invention.
Figure 7B:
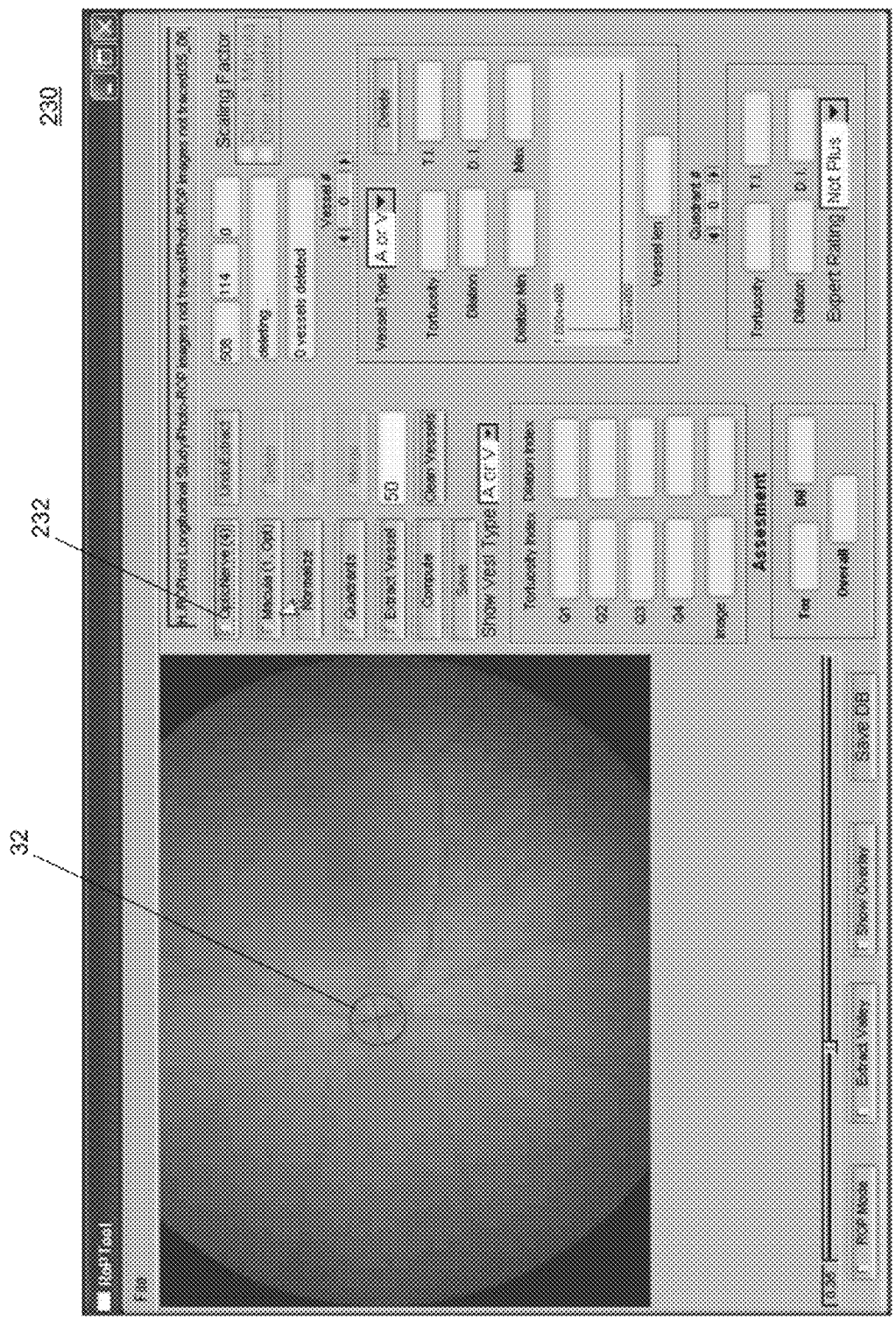
Figure 7C:
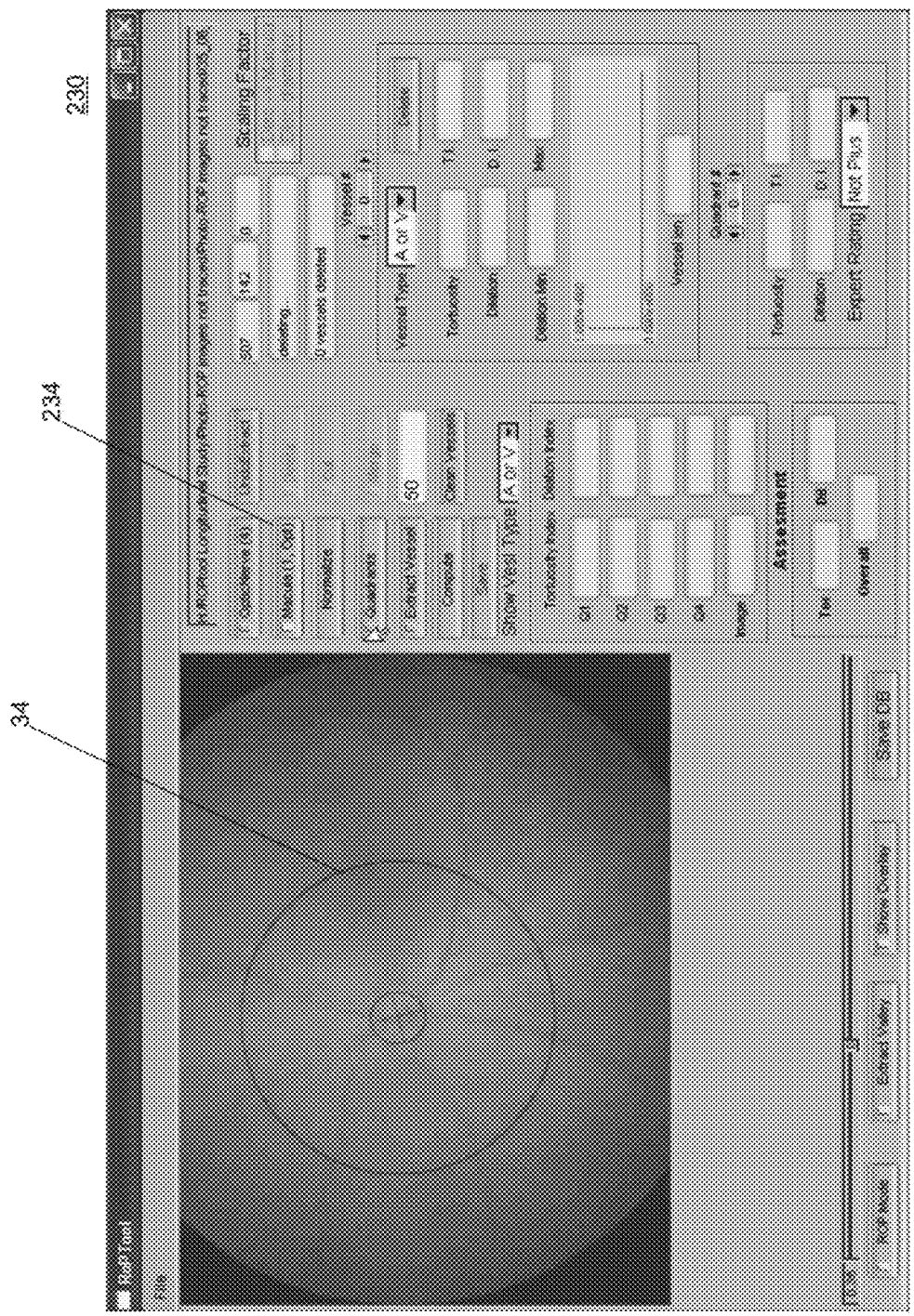
Figure 7D:
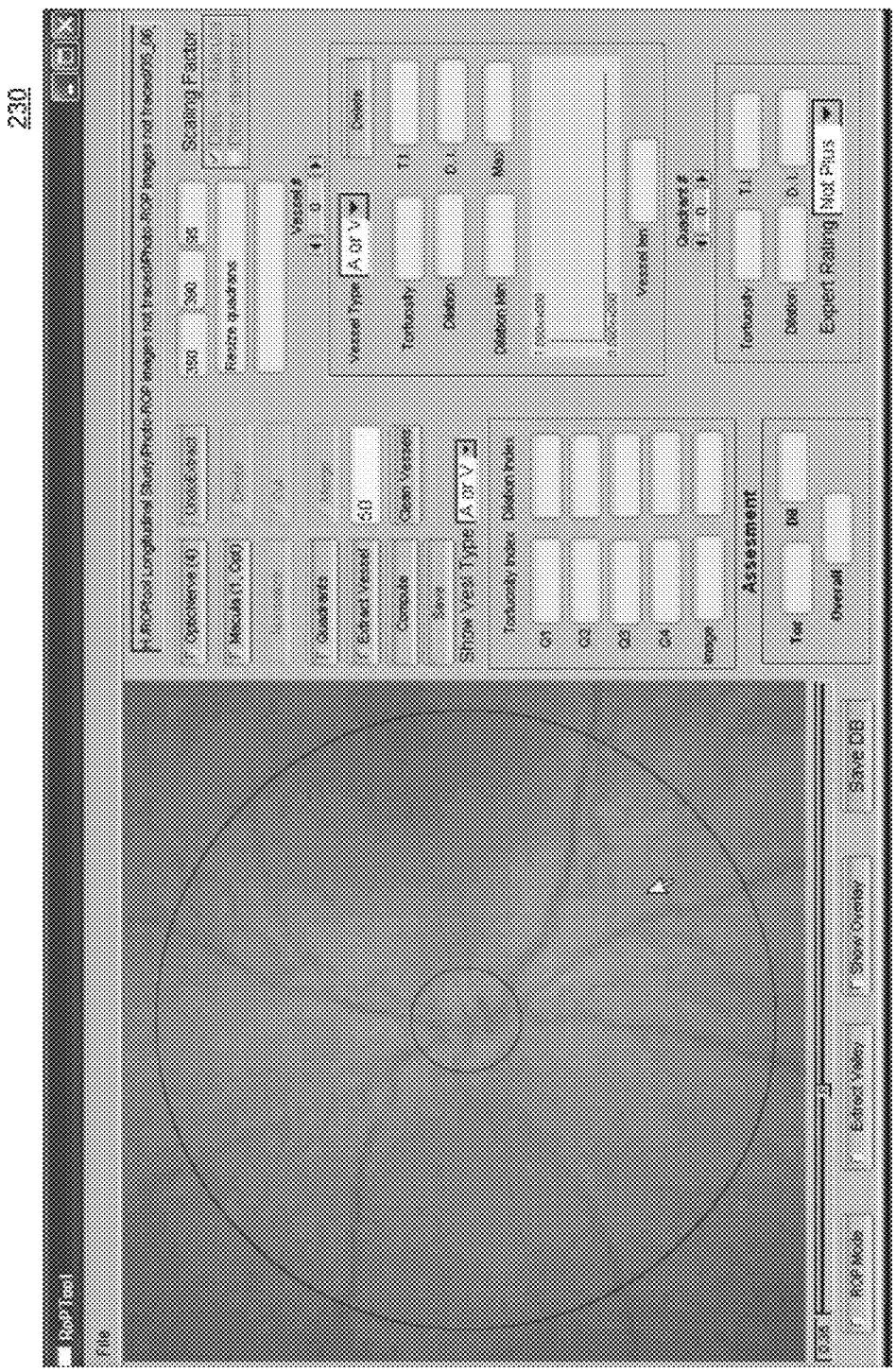
Figure 7E:
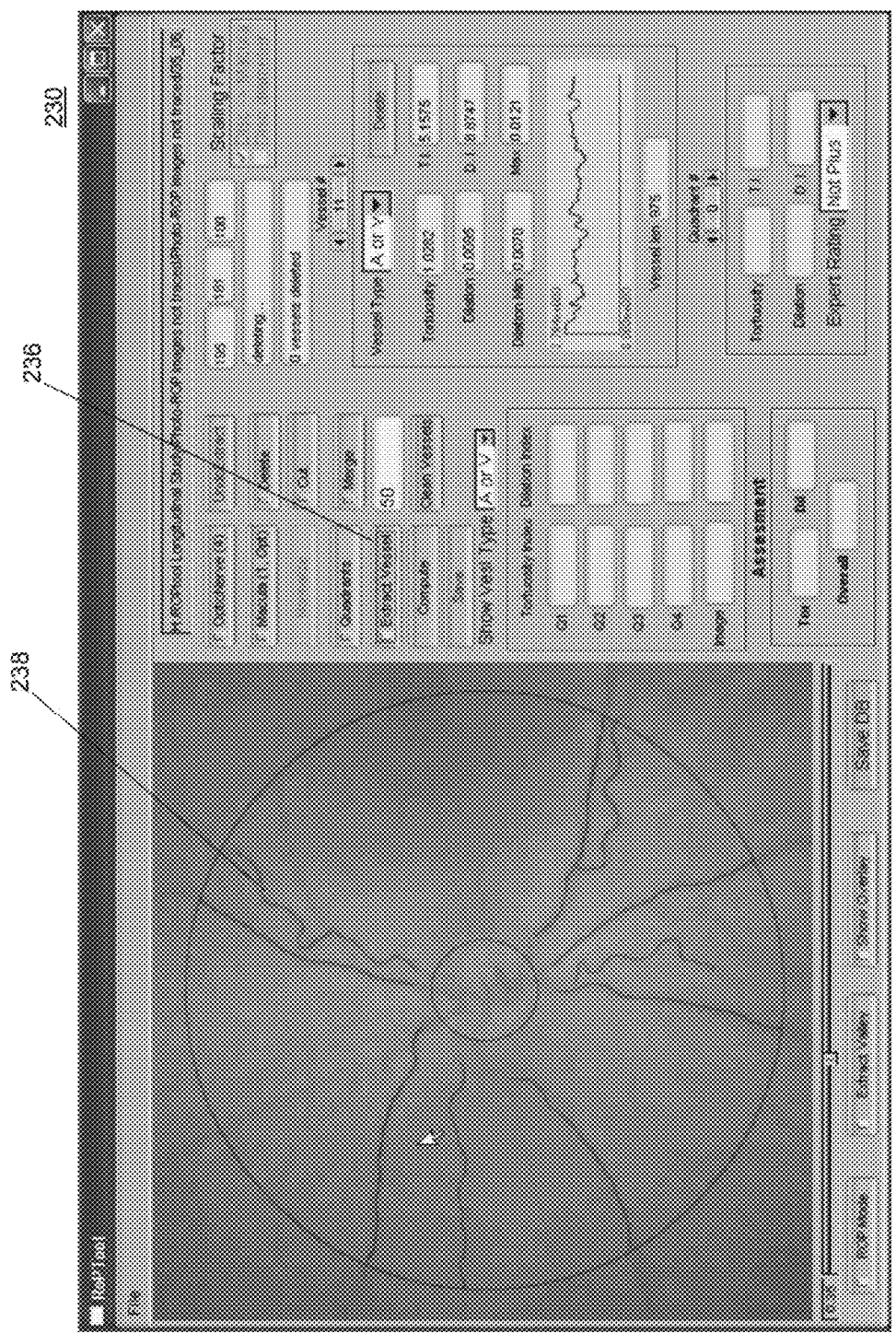
Figure 7F:
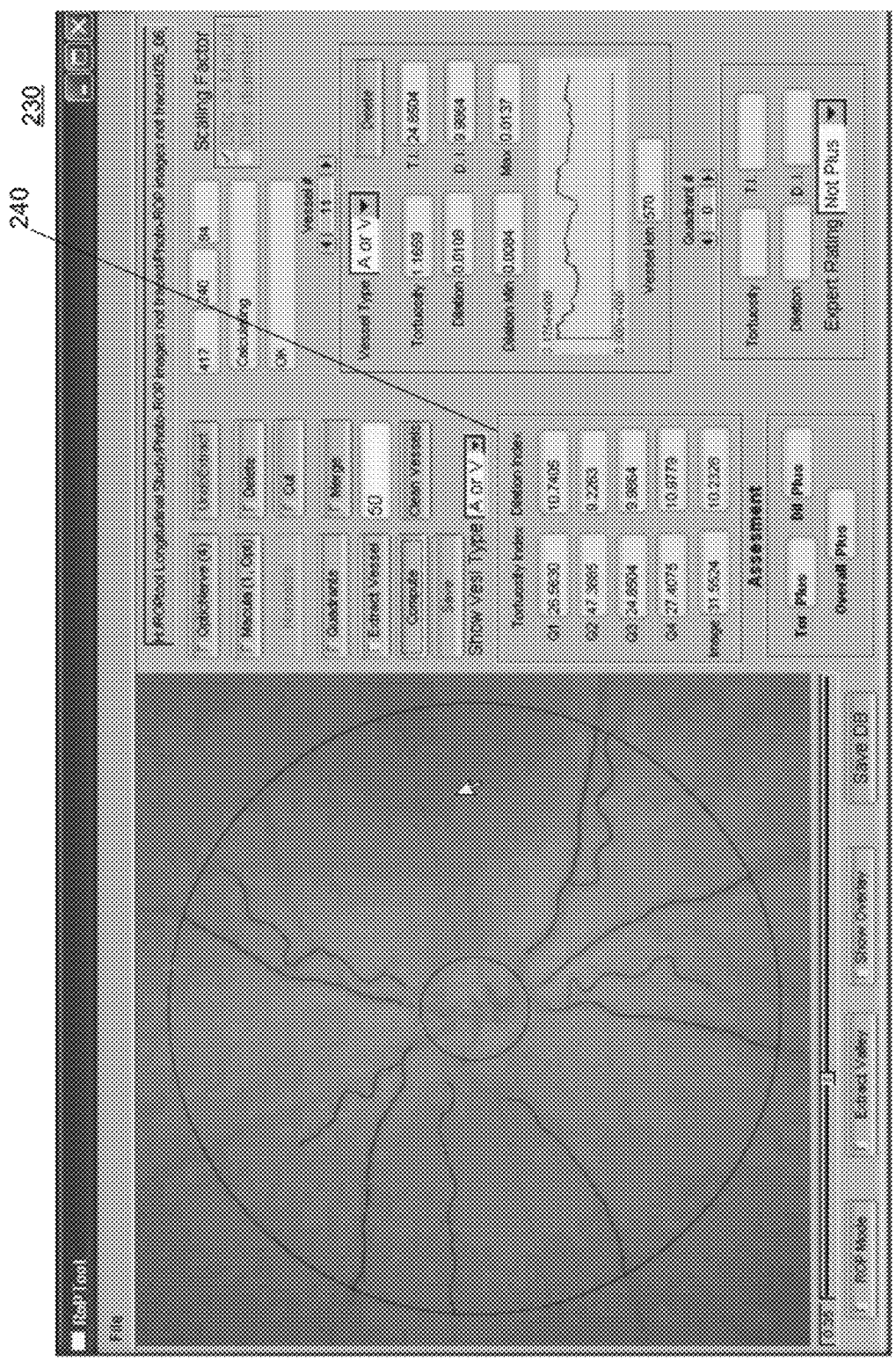
Figure 7G:
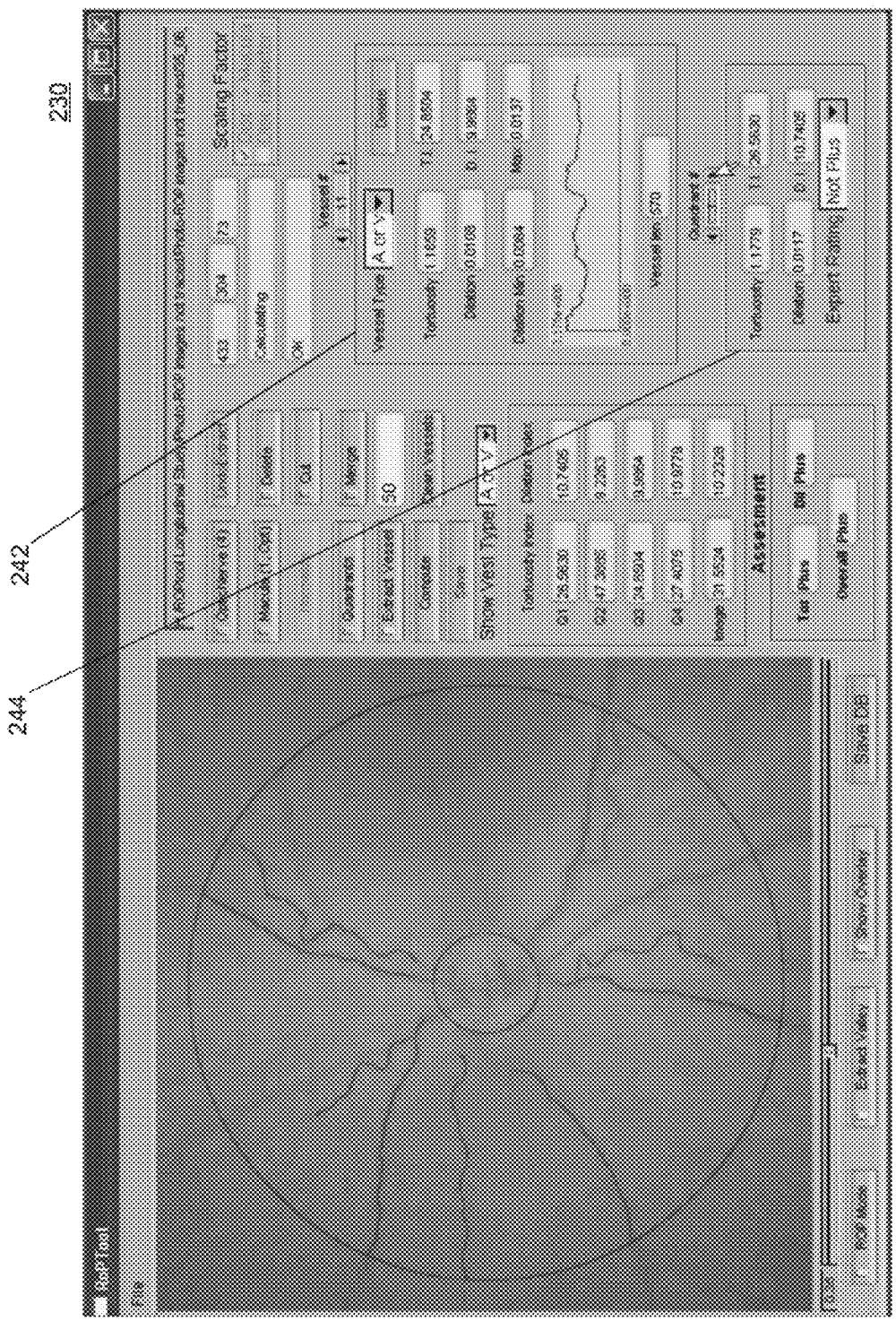

FIGS. 7A-7G are a series of screen shots of analysis tool 230 for performing automated analysis and diagnostics on the uploaded patient photo information according to an embodiment of the invention. As shown in FIG. 7B the optical nerve is circled and identified by the automated system with the selection of the optical nerve button 232. In FIG. 7C with the selection of the macula button 234, the zone 1 circle is automatically generated. FIG. 7D show an expanded view of zone 1 for improved visual diagnostics. FIG. 7E shows a highlighting tool for extracting vessels (button 236) with the vessels highlighted 238. Various parameters related to the vascular structure within zone 1 is recorded as shown in 7F where a tortuosity index and dilation index is calculated for the four quadrants and the image itself in zone 1 in box 240. In FIG. 7G tortuosity and dilation for individual vessels is shown in boxes 242 and 244. The measurements shown in FIGS. 7A-7G are used in the determination of the presence and severity of the ROP condition.

FIG. 8 is a schematic diagram illustrating an overall view of communication devices, computing devices, and mediums for implementing the automated system and method for ascribing the boundary of zone 1 in a retinograph that avoids to subjective evaluation of conventional techniques. Eye treatment follows based on the accurate determination of vasculature forming the boundary of the zone 1.

The system 300 includes multimedia devices 302 and desktop computer devices 304 configured with display capabilities 314 and processors for executing instructions and commands. The multimedia devices 302 are optionally mobile communication and entertainment devices, such as cellular phones, tablets, and mobile computing devices that in certain embodiments are wirelessly connected to a network 308. The multimedia devices 302 typically have video displays 318 and audio outputs 316. The multimedia devices 302 and desktop computer devices 304 are optionally configured with internal storage, software, and a graphical user interface (GUI) for carrying out elements of the automated diagnostic platform according to embodiments of the invention. The network 308 is optionally any type of known network including a fixed wire line network, cable and fiber optics, over the air broadcasts, satellite 320, local area network (LAN), wide area network (WAN), global network (e.g., Internet), intranet, etc. with data/Internet capabilities as represented by server 306. Communication aspects of the network are represented by cellular base station 310 and antenna 312. In a preferred embodiment, the network 308 is a LAN and each remote device 302 and desktop device 304 executes a user interface application (e.g., Web browser) to contact the server system 306 through the network 308. Alternatively, the remote devices 302 and 304 may be implemented using a device programmed primarily for accessing network 308 such as a remote client.

The software for the diagnostic platform, of embodiments of the invention, may be resident on a USB thumb or flash drive 320, CD or DVD 322, or an external hard drive 324 for connection to desktop or laptop computers 304, or stored within the server 306 or cellular base station 310 for download to an end user. Server 306 may implement a cloud-based service for implementing embodiments of the diagnostic platform with a multi-tenant database for storage of separate client data for each independent trial being carried out on the platform.

Patents and references cited in the application are indicative of the skill in the art. Each of these patents and references is hereby incorporated by reference to the same extent as if each reference was individually incorporated by reference.

The foregoing description is illustrative of particular embodiments of the invention, but is not meant to be a limitation upon the practice thereof. The following claims, including all equivalents thereof, are intended to define the scope of the invention.

The invention claimed is:

1. An automated method for diagnosing and evaluating severity of retinopathy of prematurity in a retina of a patient, said method comprising:
   providing a graphical user interface (GUI);
   receiving biographical information for the patient creating a patient record in a database via said GUI;
   receiving at least one photograph of the retina of the patient for placement in said patient record via said GUI;
   identifying a center of an optical nerve in said at least one photograph of the retina computationally;
   identifying a macula in said at least one photograph of the retina computationally;
   analyzing said at least one photograph to determine vascular distributions within the retina;
   assigning a zone 1 boundary to the retina based on a set of threshold levels with respect to the determined vascular distributions; and
   displaying said zone 1 boundary on said GUI.

2. The method of claim 1 wherein said biographical information of the patient includes at least one of a medical record number, patient name, gender, date of birth, birth weight, gestational age, and patient ethnicity.

3. The method of claim 1 further comprising providing a template with a series of boxes labeled for said at least one photograph of the retina; and
   wherein an individual photograph from said at least one photograph is dragged or dropped into a corresponding labeled box from said series of boxes.

4. The method of claim 1 wherein said at least one photograph comprise right and left eye versions of external, inferior, nasal, posterior, superior, and temporal views.

5. The method of claim 1 further comprising determining the extent of diseases of the eye based on the determined vascular distributions within the retina for said zone 1 boundary.

6. The method of claim 1 further comprising forming a montage of the retina from a series of photographs of the retina.

7. The method of claim 1 wherein the disease of the eye is retinopathy of prematurity (ROP).

8. The method of claim 1 further comprising generating reports on the extent of diseases of the eye under evaluation.

9. The method of claim 1 wherein machine learning and artificial intelligence (AI) is utilized to provide diagnostic information based on a learned history of sets of previous patient images and inputted expert analysis of the sets of previous images by physicians and researchers.

10. The method of claim 1 further comprising treating the eye based on the extent of the diseases of the eye.

11. A system for the diagnosis and evaluation of severity of retinopathy of prematurity in a retina of a patient, said system comprising:
   a server connected via a network to user devices for use by a series of users;
   a memory system in electrical communication with said server containing a machine readable medium having stored thereon one or more sequences of instructions which, when executed by a processor, cause a method to be carried out, the method comprising:
   providing a graphical user interface (GUI);
   receiving a biographical information of the patient for creating a patient record in a database via said GUI;
   receiving a series of photographs of the retina of the patient for placement in said patient record via said GUI;
   identifying a center of an optical nerve in said at least one photograph of the retina computationally;
   identifying a macula in said at least one photograph of the retina computationally;
   analyzing said series of photographs to determine vascular distributions within the retina;
   assigning a boundary of zone 1 in the retina based on a set of threshold levels with respect to the determined vascular distributions; and
   displaying said zone 1 boundary on said GUI.

12. The system of claim 11 wherein said biographical information of the patient at least one of medical record number, patient name, gender, date of birth, birth weight, gestational age, and patient ethnicity.

13. The system of claim 11 further comprising a template with a series of boxes labeled for the series of photographs of the retina; and
   wherein an individual photograph from the series of photographs is dragged or dropped into a corresponding labeled box from said series of boxes.

14. The system of claim 11 wherein said series of photographs comprise right and left eye versions of external, inferior, nasal, posterior, superior, and temporal views.

\* \* \* \* \*